US009776949B2

(12) United States Patent
Kaller et al.

(10) Patent No.: US 9,776,949 B2
(45) Date of Patent: Oct. 3, 2017

(54) PROCESS FOR THE PRODUCTION OF CARBOXYLIC ESTERS AND USE OF THESE AS PLASTICIZERS

(71) Applicant: BASF SE, Ludwigshafen (DE)

(72) Inventors: Martin Kaller, Mannheim (DE); Michael Koch, Speyer (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/305,932

(22) PCT Filed: Apr. 20, 2015

(86) PCT No.: PCT/EP2015/058482
§ 371 (c)(1),
(2) Date: Oct. 21, 2016

(87) PCT Pub. No.: WO2015/162079
PCT Pub. Date: Oct. 29, 2015

(65) Prior Publication Data
US 2017/0044085 A1    Feb. 16, 2017

(30) Foreign Application Priority Data

Apr. 22, 2014 (EP) ..................... 14165458

(51) Int. Cl.
| | | |
|---|---|---|
| *C07C 67/08* | (2006.01) | |
| *C07C 67/54* | (2006.01) | |
| *C08K 5/00* | (2006.01) | |
| *C08K 5/10* | (2006.01) | |
| *C08K 5/12* | (2006.01) | |

(52) U.S. Cl.
CPC ............. *C07C 67/08* (2013.01); *C07C 67/54* (2013.01); *C08K 5/0016* (2013.01); *C08K 5/10* (2013.01); *C08K 5/12* (2013.01)

(58) Field of Classification Search
CPC .................. C07C 67/08; C08K 5/12
See application file for complete search history.

(56) References Cited

U.S. PATENT DOCUMENTS

| | | |
|---|---|---|
| 1,923,938 A | 8/1933 | Kyrides |
| 2,628,207 A | 2/1953 | Smith, Jr. et al. |
| 2,921,089 A | 1/1960 | Hagemeyer, Jr. et al. |
| 4,148,830 A | 4/1979 | Pruett et al. |
| 4,426,524 A | 1/1984 | Plummer |
| 5,288,918 A | 2/1994 | Maher et al. |
| 5,434,313 A | 7/1995 | Harrison et al. |
| 7,799,942 B2 | 9/2010 | Osborne et al. |
| 2011/0251420 A1 | 10/2011 | Disteldorf et al. |
| 2015/0141691 A1 | 5/2015 | Disteldorf et al. |

FOREIGN PATENT DOCUMENTS

| | | |
|---|---|---|
| CN | 102001948 A | 4/2011 |
| CN | 102329233 A | 1/2012 |
| CN | 102824929 A | 12/2012 |
| DE | 24 04 855 A1 | 8/1775 |
| DE | 1 593 368 A1 | 7/1970 |
| DE | 2 139 630 A1 | 2/1973 |
| DE | 2 244 373 A1 | 4/1974 |
| DE | 24 45 303 A1 | 4/1976 |
| DE | 26 28 987 A1 | 1/1978 |
| DE | 32 28 881 A1 | 2/1984 |
| EP | 0 366 089 A2 | 5/1990 |
| EP | 0 695 734 A1 | 2/1996 |
| EP | 0 880 494 B1 | 5/2000 |
| EP | 1 047 655 B1 | 5/2003 |
| JP | 62-267341 A | 11/1987 |
| WO | WO 95/14647 A1 | 6/1995 |
| WO | WO 98/23566 A1 | 6/1998 |
| WO | WO 00/50351 A1 | 8/2000 |
| WO | WO 01/14297 A1 | 3/2001 |
| WO | WO 01/87809 A1 | 11/2001 |
| WO | WO 02/083695 A1 | 10/2002 |
| WO | WO 2005/028407 A1 | 3/2005 |
| WO | WO 2008/123928 A1 | 10/2008 |
| WO | WO 2010/076192 A1 | 7/2010 |

OTHER PUBLICATIONS

International Search Report issued Jul. 30, 2015 in PCT/EP2015/058482.
International Preliminary Report on Patentability issued Aug. 25, 2016 in PCT/EP2015/058482 filed Apr. 20, 2015.
David F. Cadogan, et al., "Plasticizers" Ullmann's Encyclopedia of Industrial Chemistry, vol. 27, XP055167665, 2012, pp. 599-618.
Peter M. Lorz, et al., "Phthalic Acid and Derivatives" Ullmann's Encyclopedia of Industrial Chemistry, vol. 27, XP055167648, 2012, pp. 131-180.
OXEA GmbH, "Oxsoft/Oxblue Brochure" Retrieved from the Internet:URL: http://ox-rch.by.nf/fileadmin/phthalate/OXSOFT/OXSOFT_OXBLUE-Bruchure.pdf, XP055202678, Feb. 2014, pp. 1-20.
Hua-Ping Zhu, et al. "Brønsted Acidic Ionic Liquid 1-Methylimidazolium Tetrafluoroborate: a Green Catalyst and Recyclable Medium for Esterification" Green Chemistry, vol. 5, No. 1, XP55203035, Jan. 1, 2003, pp. 38-39.
Hoang-Phuong Nguyen, et al., "An Improved Greener Esterification of Fatty Alcohols Using a Renewable Acid-Ionic Liquid Couple as Catalyst-Solvent" Synthetic Communications, vol. 34, No. 11, XP8086678, Jan. 1, 2004, pp. 2085-2093.
Yue Qin Cai, et al., "Imidazolium Ionic Liquid-Supported Sulfonic Acids: Efficient and Recyclable Catalysts for Esterification of Benzoic Acid" Chinese Chemical Letters, vol. 23, No. 1, XP028393378, 2012, pp. 1-4.

(Continued)

*Primary Examiner* — Yevegeny Valenrod
*Assistant Examiner* — Blaine G Doletski
(74) *Attorney, Agent, or Firm* — Oblon, McClelland, Maier & Neustadt, L.L.P.

(57) ABSTRACT

The invention relates to a method for producing carboxylic acid esters by reacting carboxylic acids and/or carboxylic acid anhydrides with at least one alcohol having at least 5 carbon atoms, selected from alkanols and cycloalkanols, in the presence of an ionic liquid and an acidic esterification catalyst. The invention also relates to the use of the thus obtained carboxylic acid esters as a plasticizer or in a plasticizer composition for thermoplastic polymers and elastomers.

19 Claims, No Drawings

(56) References Cited

OTHER PUBLICATIONS

Congxia Xie, et al., "Synthesis of Plasticizer Ester Using Acid-Functionalized Ionic Liquid as Catalyst" Journal of Hazardous Materials, vol. 151, No. 2-3, XP022450980, Dec. 4, 2007, pp. 847-850.

"Fluka-Riedel-de Haën Katalog: Laborchemikalien and analytische Reagentien 2005/2006" Sigma-Aldrich, XP055203357, Jan. 1, 2005, pp. 756, 757, 1005, 1006 and cover page.

PROCESS FOR THE PRODUCTION OF CARBOXYLIC ESTERS AND USE OF THESE AS PLASTICIZERS

BACKGROUND OF THE INVENTION

The present invention relates to a process for the production of carboxylic esters by reaction of carboxylic acids and/or carboxylic anhydrides with at least one alcohol having at least 5 carbon atoms, selected among alkanols and cycloalkanols, in the presence of an ionic liquid and of an acidic esterification catalyst. The invention further relates to the use of the resultant carboxylic esters as plasticizers or in a plasticizer composition for thermoplastic polymers and elastomers.

PRIOR ART

Esters of aliphatic and aromatic carboxylic acids with alkanols and cycloalkanols having at least 5 carbon atoms are widely used in industry. They are by way of example widely used in surface-coating resins and as constituents of paints, and it is specifically the esters of phthalic acid, trimellitic acid, terephthalic acid, adipic acid, sebacic acid, or maleic acid that are used here. They are moreover specifically suitable as plasticizers or as component of a plasticizer composition for thermoplastic polymers and elastomers.

Plasticizers are added to a wide variety of plastics in order to achieve the desired processing properties or the desired usage properties, the aim being to render the plastics softer, more flexible, and/or more extensible. The use of plasticizers generally serves to shift the thermoplastic range of plastics toward lower temperatures, so that the desired resilient properties can be obtained in the region of low processing temperatures and low usage temperatures. Important thermoplastic polymers in which plasticizers are usually used are not only polyvinyl chloride (PVC) but also by way of example polyvinyl butyral (PVB), styrene homo- and copolymers, polyacrylates, polysulfides, and thermoplastic polyurethanes (PU). Materials that have been widely used as plasticizers in the past because of their good compatibility with PVC and with other polymers, and because of their advantageous performance characteristics, are phthalic diesters with alcohols of varying chemical structure, an example being diethylhexyl phthalate (DEHP). However, these give rise to some toxicological concerns and in recent times they have been replaced by other plasticizers specifically for sensitive application sectors such as toys, food packaging, and medical items. Particular materials of importance here are the esters of other aromatic carboxylic acids, for example of terephthalic acid, trimellitic acid, and benzoic acid.

It is known that carboxylic esters can be produced by reaction of carboxylic acids with alcohols. This reaction can be carried out autocatalytically or with catalysis, for example by Brønsted acids or by Lewis acids. Processes of this type are described in Lorz et al., Phthalic Acid and Derivatives, Ullmann's Encyclopedia of Industrial Chemistry, 2007, pages 131-180 (DOI: 10.1002/14356007.a20_181.pub2). In the case of autocatalytic esterification the reaction temperatures are usually >200° C. Nevertheless, conversions achieved are generally only partial, and recycling of the residual carboxylic acid is therefore essential.

Irrespective of the nature of the catalysis, there is always a resultant temperature-dependent equilibrium between the starting materials (carboxylic acid and alcohol) and the products (ester and water). The reaction of internal carboxylic anhydrides with alcohols proceeds in two steps: alcoholysis of the anhydride to give the monoester generally proceeds rapidly and to completion. Further reaction of the monoester to give the diester with formation of water of reaction is reversible and proceeds slowly. This second step is the rate-determining step of the reaction. In order to shift the equilibrium in favor of the ester (or of the full ester in the case of polybasic acids), an entrainer is generally used to remove the water of reaction from the mixture. If one of the starting materials (alcohol or carboxylic acid) has a lower boiling point than the resultant ester and has a region of emiscibility with water, a starting material can be used as entrainer and, after removal of water, can be returned to the mixture. In the case of esterification of higher aliphatic carboxylic acids, aromatic carboxylic acids, or di- or polybasic carboxylic acids, the entrainer is generally the alcohol used.

Typical esterification catalysts for the production of carboxylic esters suitable as plasticizers are tetraalkyl titanates.

U.S. Pat. No. 7,799,942 by way of example discloses a process for the production of diesters of terephthalic acid, for example bis(2-ethylhexyl) terephthalate (DOTP) in which terephthalic acid and a $C_6$-$C_{10}$-alcohol are subjected to esterification in the presence of a tetraalkyl titanate as catalyst, where the water produced during the esterification reaction, and a portion of the alcohol, are removed by passing an inert gas through the reaction zone, or with the aid of a distillation column.

The use of tetraalkyl titanates as catalysts has a number of attendant disadvantages: in order to remove the catalyst, a base, for example aqueous NaOH, is admixed with the reaction mixture, and the resultant hydrolysis products are removed by filtration. This removal is time-consuming, and space-time yields achieved are therefore low. Further work-up of the reaction mixture is generally required, for example distillation for the removal of excess alcohol and/or treatment with activated carbon in order to achieve acceptable color values.

Other materials described in the prior art as catalysts for the production of carboxylic esters are mineral acids and strong organic acids, for example methanesulfonic acid and p-toluenesulfonic acid. However, Lorz et al., Phthalic Acid and Derivatives, Ullmann's Encyclopedia of Industrial Chemistry, 2007, pages 131-180 (DOI: 10.1002/14356007.a20_181.pub2) teaches that Brønsted acid catalysts, such as sulfuric acid or sulfonic acids, can be used only up to a temperature of 165° C., since otherwise disruptive side reactions occur and can lead to formation of ethers, sulfonic esters, olefins (through elimination of water from the alcohols used) or to other byproducts which discolor the esterification products in an undesired manner.

JP 62267341 discloses a process for the production of carboxylic esters for use as plasticizers, obtainable by reaction of a carboxylic acid with an alcohol in the presence of a sulfonic acid as esterification catalyst. The crude esterification product here is subjected to purification by addition of a base, e.g. CaO or MgO, and of a solid adsorbent, for example activated carbon, kieselguhr, or activated bleaching earth, in order to reduce the acid number and, respectively, the color value.

WO 2008/123928 describes a process for the production of di(n-butyl) terephthalate from terephthalic acid and n-butanol, where the esterification reaction is carried out with a 1.25- to 4-fold molar excess of n-butanol at atmospheric pressure and at a reaction temperature of from 110 to 220°

C. with use of an esterification catalyst. Specifically, because the boiling point of n-butanol is 117° C., this process is preferably carried out at a reaction temperature of from 115 to 150° C. (i.e. in essence at reflux), preference being given here to use of a sulfonic acid or sulfuric acid as esterification catalyst. n-Butanol is continuously introduced into the reaction zone during the reaction. The water produced during the reaction is extracted by distillation in the form of azeotropic mixture. In some of the embodiments, nitrogen is passed through the reaction mixture, but this measure has no discernible favorable effect on the yield, purity, or color value of the resultant esterification product.

Generally speaking, the Brønsted acids used as catalyst in these processes, such as sulfonic acids or sulfuric acid, have to be removed at the end of the reaction in a basic scrub, and consequently cannot be used again.

Esterification processes in which ionic liquids are employed are likewise known in the prior art.

CN102001948A describes a process for preparing diisooctyl terephthalate (DOTP) from terephthalic acid and 2-ethylhexanol, where the esterification catalyst used is an ionic liquid obtainable from the reaction of 1-butylpyridinium chloride with tin(II) chloride.

CN102824929A describes a process for preparing diisooctyls terephthalate (DOTP) from terephthalic acid and 2-ethylhexanol, where a catalyst system is used that consist of two catalysts, catalyst 1 and catalyst 2. Catalyst 1 is a mixture of an ionic liquid and a metal compound. The ionic liquid here is selected from imidazolium or benzimidazolium ions, which may carry a sulfate, bisulfate or nitrate counterion and may be substituted optionally by sulfonic acid groups. Catalyst 2 is a mixture of a titanium metal compound and a further metal compound. In the process, specifically, catalyst 1 is added to a mixture of the two reactants at a reaction temperature of 130 to 150° C., followed by the addition of catalyst 2 after a further temperature increase to 160 to 220° C., the reaction being stirred under reflux for a further 0.5 to 3 hours, and the water formed during the reaction being taken off by distillation in the form of an azeotropic mixture.

CN102329233A describes a process for synthesizing diisooctyl terephthalate (DOTP) by an esterification reaction in which terephthalic acid and 2-ethylhexanol are reacted in the presence of tetrabutyl titanate as primary esterification catalyst and of an ionic liquid consisting of a quaternary ammonium salt, as co-catalyst and solubilizer.

In many cases, the carboxylic acids used for preparing plasticizers, such as terephthalic acid, are only poorly soluble in the alcohols used for the esterification, such as 2-ethylhexanol, for example. This increases the risk of formation of byproducts in the conventional titanium-catalyzed or acid-catalyzed esterification processes, since long reaction times and/or elevated reaction temperatures are needed in order to obtain high conversions.

The present invention is based on the object of providing an improved process for the production of carboxylic esters which are suitable for a use as plasticizer. The intention here is preferably to achieve conversion that is as far as possible complete after a short reaction time, and thus to achieve a high space-time yield, with the intention being to simultaneously minimize the formation of byproducts. A further intention is that it be possible to carry out the process at low cost and in a technically simple manner, e.g. by using an inexpensive catalyst and by avoiding complicated work-up steps, thus permitting substantial avoidance of the disadvantages described above which result inter alia from the use of metal compounds, such as tetraalkyl titanates, as esterification catalysts. In addition, the process should make it possible to recycle the catalyst. The resultant carboxylic esters are nevertheless intended to feature good product properties, specifically for a use as plasticizer. These include, for applications in sectors where the optical properties of the plasticized plastics are important, minimized coloring of the carboxylic esters, apparent by way of example in a low color value.

Surprisingly, it has now been found that this object is achieved when the esterification reaction for the production of the carboxylic esters suitable as plasticizers is carried out at high temperatures in the presence of an organic sulfonic acid, specifically methanesulfonic acid, as catalyst, and in the presence of an ionic liquid, where the alcohol used for the esterification reaction serves as entrainer for the resultant water of reaction and, after water removal, is returned to the reaction. In one specific embodiment, methanesulfonic acid with low total chlorine content and low sulfate content is used as catalyst.

BRIEF DESCRIPTION OF THE INVENTION

The invention provides a process for the production of carboxylic esters, by reaction of at least one carboxylic acid and/or at least one carboxylic anhydride and at least one alcohol $R^1$—OH, in which $R^1$ is selected among unbranched and branched saturated $C_5$-$C_{13}$-alkyl moieties and $C_5$-$C_6$-cycloalkyl moieties, where the cycloalkyl moieties are unsubstituted or may be substituted by at least one $C_1$-$C_{10}$-alkyl moiety, with the proviso that the reaction takes place in the presence of at least one ionic liquid which is selected from among salts of the general formula (I),

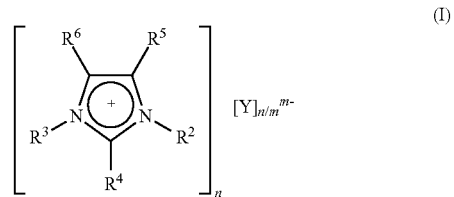

in which radicals $R^2$ and $R^3$, independently of one another, are hydrogen, or are in each case unsubstituted or substituted alkyl, alkenyl, cycloalkyl, cycloalkenyl, polycyclyl, heterocycloalkyl, aryl or heteroaryl, radicals $R^4$, $R^5$, and $R^6$, independently of one another, are hydrogen, or are in each case unsubstituted or substituted alkyl, alkenyl, cycloalkyl, cycloalkenyl, polycyclyl, heterocycloalkyl, aryl, heteroaryl, alkoxy, cycloalkyloxy, cycloalkenyloxy, alkylsulfinyl, alkylsulfonyl, acyl or $NE^1E^2$, where $E^1$ and $E^2$ independently of one another are hydrogen, alkyl, cycloalkyl, heterocycloalkyl, aryl or hetaryl, where the carbon chains of the alkyl groups of the radicals $R^2$ to $R^6$ independently of one another may be interrupted by one or more nonadjacent heteroatoms or heteroatom-containing groups, which are preferably selected from —O—, —S—, —$NR^a$—, —$PR^a$—, —$SiR^aR^b$ and/or —$SO_2$—, where $R^a$ and $R^b$ are preferably hydrogen, alkyl, cycloalkyl, heterocycloalkyl or aryl, or two adjacent radicals $R^2$ to $R^6$, together with the ring atoms to which they are bonded, may also be at least one fused, saturated, unsaturated or aromatic ring or a ring system having 1 to 30 carbon atoms, it being possible for the ring or ring system to have 1 to 5 nonadjacent heteroatoms or heteroatom-containing groups, and to be unsubstituted or substituted,

[Y]$^{m-}$— is an m-valent multiatomic anion, where m has values of 1, 2, 3 or 4, and n has values of 1, 2, 3 or 4, in the presence of at least one catalyst selected among organic sulfonic acids, and with distillative removal, in the form of an azeotropic mixture with the alcohol R$^1$—OH used, of at least one portion of the water formed during the reaction, where at least to some extent the alcohol R$^1$—OH removed by distillation is returned to the reaction system.

In one specific embodiment, the process of the invention serves for the production of esters of terephthalic acid, very specifically for the production of bis(2-ethylhexyl) terephthalate (DOTP).

The invention further provides the use of the resultant carboxylic esters as plasticizers or as component in a plasticizer composition for thermoplastic polymers and elastomers.

DESCRIPTION OF THE INVENTION

The process of the invention has the following advantages:

It is possible to produce carboxylic esters suitable as plasticizers in short reaction times, i.e. with high space-time yield.

Despite the relatively severe reaction conditions, the carboxylic esters are obtained in high yields and with good selectivities.

Although a Brønsted acid is used as catalyst, extremely little formation of undesired byproducts, specifically of sulfonic esters or ethers of the alcohol used for the esterification reaction, and of olefins from elimination of water from the alcohol, is observed.

The ionic liquid used in the esterification process according to the invention advantageously acts as solubilizer between the carboxylic acid and the alcohol, as a result of which the reaction time can be reduced.

The Brønsted acid used as catalyst may be removed together with the ionic liquid from the reaction mixture, and used again for further esterification reactions.

It is generally possible to omit the use of complicated measures for purification of the carboxylic esters obtained according to the process of the invention. This applies specifically to the use of adsorbents for obtaining less-colored products.

It is generally possible to omit the use of external organic solvents, i.e. the use of components which act as solvents and which differ from the starting materials used for the production of the carboxylic esters and from the products formed in the reaction.

The process of the invention is specifically suitable for the production of esters of terephthalic acid, trimellitic acid, and benzoic acid, and of esters of alicyclic and aliphatic carboxylic acids which because of their advantageous toxicological properties are of great importance for use as plasticizers.

The resultant carboxylic esters have no, or only slight, coloring, and feature a low Hazen color value (determinable in accordance with DIN/EN/ISO 6271-2). This is generally at least as good as, or better than, that of products which are obtained by the substantially more complicated process by means of catalysis by tetraalkyl titanates.

For the purposes of the present invention, the expression "reaction system" refers to the entirety of all of the reactants, solvents, and catalysts supplied to the reaction, and also the products and intermediates formed in the reaction.

For the purposes of the present invention, the expression "alkyl" comprises unsubstituted straight-chain or branched alkyl groups which comprise from 1 to 30 carbon atoms, preferably from 1 to 20 carbon atoms. These are particularly preferably unsubstituted straight-chain or branched $C_1$-$C_{13}$-alkyl groups, particularly preferably unsubstituted straight-chain or branched $C_1$-$C_6$-alkyl groups. Among the unsubstituted straight-chain or branched $C_1$-$C_{13}$-alkyl groups are methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 1-ethylpentyl, 2-ethylpentyl, 1-propylbutyl, 1-ethyl-2-methylpropyl, n-octyl, isooctyl, 2-ethylhexyl, n-nonyl, isononyl, 2-propylhexyl, n-decyl, isodecyl, 2-propylheptyl, n-undecyl, isoundecyl, n-dodecyl, isododecyl, n-tridecyl and isotridecyl, and the like.

The expression "alkyl" also includes in its definition the expressions "$C_5$-$C_{13}$-alkyl", "$C_1$-$C_{10}$-alkyl" and "$C_1$-$C_6$-alkyl".

The carbon chain of the alkyl radicals may be interrupted by one or more nonadjacent heteroatoms or heteroatom-comprising groups. Alkyl radicals whose carbon chains are interrupted by one or more nonadjacent heteroatoms or heteroatom-comprising groups are selected from those alkyl radicals that are interrupted by —O—, —S—, —NR$^a$—, —PR$^a$—, —SiR$^a$R$^b$ and/or —SO$_2$—. R$^a$ and R$^b$ are preferably hydrogen, alkyl, cycloalkyl, heterocycloalky or aryl.

Examples of alkyl radicals whose carbon chains may be interrupted by one or two nonadjacent heteroatoms —O— are the following:

methoxymethyl, diethoxymethyl, 2-methoxyethyl, 2-ethoxyethyl, 2-propoxyethyl, diethoxyethyl, 2-butoxyethyl, 2-octyloxyethyl, 2-methoxypropyl, 3-methoxypropyl, 3-ethoxypropyl, 3-propoxypropyl, 2-isopropoxyethyl, 2-butoxypropyl, 3-butoxypropyl, 4-methoxybutyl, 4-ethoxybutyl, 4-propoxybutyl, 6-methoxyhexyl, 3,6-dioxaheptyl (5-methoxy-3-oxapentyl), 3,6-dioxaoctyl (7-methoxy-4-oxaheptyl), 4,8-dioxanonyl (7-methoxy-4-oxaheptyl), 3,7-dioxaoctyl, 3,7-dioxanonyl, 4,7-dioxaoctyl, 4,7-dioxanonyl, 2- and 4-butoxybutyl, 4,8-dioxadecyl, 9-ethoxy-5-oxanonyl.

Examples of alkyl radicals whose carbon chains may be interrupted by three or more than three nonadjacent heteroatoms —O— also include oligooxyalkylenes and polyoxyalkylenes, i.e. compounds having repeating units which are preferably selected from among $(CH_2CH_2O)_{x1}$, $(CH(CH_3)CH_2O)_{x2}$ and $((CH_2)_4O)_{x3}$, where x1, x2 and x3 are each, independently of one another, an integer from 3 to 100, preferably from 3 to 80. The sum of x1, x2 and x3 is an integer from 3 to 300, in particular from 3 to 100. In polyoxyalkylenes which have two or three different repeating units, the repeating units can be present in any order, i.e. the repeating units can be randomly distributed, alternating or arranged in blocks. Examples are 3,6,9-trioxadecyl, 3,6,9-trioxaundecyl, 3,6,9-trioxadodecyl, 4,8,12-trioxatridecyl (11-methoxy-4,8-dioxaundecyl), 4,8,12-tri-oxatetradecyl, 14-methoxy-5,10-dioxatetradecyl, 5,10,15-trioxaheptadecyl, 3,6,9,12-tetraoxatridecyl, 3,6,9,12-tetraoxatetradecyl, 4,8,12,16-tetraoxaheptadecyl (15-methoxy-4,8,12-trioxapentadecyl), 4,8,12,16-tetraoxaoctadecyl and the like.

Examples of alkyl radicals whose carbon chains may be interrupted by one or more, e.g. 1, 2, 3, 4 or more than 4, nonadjacent heteroatoms —S— are the following:

butylthiomethyl, 2-methylthioethyl, 2-ethylthioethyl, 2-propylthioethyl, 2-butylthioethyl, 2-dodecylthioethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl.

Examples of alkyl radicals whose carbon chains are interrupted by one or two nonadjacent heteroatom-comprising groups —NR$^a$— are the following:

2-monomethyl- and 2-monoethylaminoethyl, 2-dimethylaminoethyl, 3-methylamino-propyl, 2- and 3-dimethylaminopropyl, 3-monoisopropylaminopropyl, 2- and 4-monopropylaminobutyl, 2- and 4-dimethylaminobutyl, 6-methylaminohexyl, 6-dimethylaminohexyl, 6-methyl-3,6-diazaheptyl, 3,6-dimethyl-3,6-diazaheptyl, 3,6-diazaoctyl and 3,6-dimethyl-3,6-diazaoctyl.

Examples of alkyl radicals whose carbon chains may be interrupted by three or more than three nonadjacent heteroatom-comprising groups —NR$^a$— also include oligoalkylenimines and polyalkylenimines. What has been said above with regard to the polyoxyalkylenes applies analogously to polyalkylenimines, with the oxygen atom being replaced in each case by an NR$^a$ group, where R$^a$ is preferably hydrogen or $C_1$-$C_4$-alkyl. Examples are 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl, 3,6,9,12-tetramethyl-3,6,9,12-tetraazatridecyl and the like.

Examples of alkyl radicals whose carbon chains are interrupted by one or more, e.g. 1 or 2, nonadjacent groups —SO$_2$— are 2-methylsulfonylethyl, 2-ethylsulfonylethyl, 2-propylsulfonylethyl, 2-isopropylsulfonylethyl, 2-butylsulfonylethyl, 2-methylsulfonylpropyl, 3-methylsulfonylpropyl, 2-ethylsulfonylpropyl, 3-ethylsulfonylpropyl, 2-propylsulfonylpropyl, 3-propylsulfonylpropyl, 2-butylsulfonylpropyl, 3-butylsulfonylpropyl, 2-methylsulfonylbutyl, 4-methylsulfonylbutyl, 2-ethylsulfonylbutyl, 4-ethylsulfonylbutyl, 2-propylsulfonylbutyl, 4-propylsulfonylbutyl and 4-butylsulfonylbutyl.

The alkyl groups can, depending on the length of the alkyl chain, have one or more (e.g. 1, 2, 3, 4, 5 or more than 5) substituents. These are preferably selected independently of one another from among cycloalkyl, cycloalkyloxy, polycyclyl, polycyclyloxy, heterocycloalkyl, aryl, aryloxy, hetaryl, halogen=O, NE$^1$E$^2$, nitro and cyano, where E$^1$ and E$^2$ are each, independently of one another, hydrogen, alkyl, cycloalkyl, heterocycloalkyl, aryl or hetaryl. Cycloalkyl, cycloalkyloxy, polycycloalkyl, polycyclyloxy, heterocycloalkyl, aryl and hetaryl substituents on the alkyl groups may in turn be unsubstituted or substituted; suitable substituents are those mentioned below for these groups.

What has been said above with regard to alkyl also applies in principle to the alkyl parts of alkoxy, alkylamino, dialkylamino, alkylsulfinyl, alkylsulfonyl, etc.

Suitable substituted alkyl radicals are the following:

Alkyl which is substituted by amino, e.g. 2-aminoethyl, 2-aminopropyl, 3-aminopropyl, 4-aminobutyl, 6-aminohexyl and the like.

Alkyl which is substituted by cyano, e.g. 2-cyanoethyl, 3-cyanopropyl, 3-cyanobutyl and 4-cyanobutyl;

Alkyl which is substituted by halogen as defined below, with some or all of the hydrogen atoms in the alkyl group being able to be replaced by halogen atoms, for example $C_1$-$C_{18}$-fluoroalkyl, e.g. trifluoromethyl, difluoromethyl, fluoromethyl, penta-fluoroethyl, heptafluoropropyl, heptafluoroisopropyl, nonafluorobutyl, nonafluoro-isobutyl, undecylfluoropentyl, undecylfluoroisopentyl and the like, C-Cis-chloroalkyl, e.g. chloromethyl, dichloromethyl, trichloromethyl, 2-chloroethyl, 2- and 3-chloropropyl, 2-, 3- and 4-chlorobutyl, 1,1-dimethyl-2-chloroethyl and the like.

Alkyl which is substituted by nitro, e.g. 2-nitroethyl, 2- and 3-nitropropyl and 2-, 3- and 4-nitrobutyl and the like.

Alkyl which is substituted by cycloalkyl, e.g. cyclopentylmethyl, 2-cyclopentylethyl, 3-cyclopentylpropyl, cyclohexylmethyl, 2-cyclohexylethyl, 3-cyclohexylpropyl and the like.

Alkyl which is substituted by =O (oxo group), e.g. 2-oxopropyl, 2-oxobutyl, 3-oxobutyl, 1-methyl-2-oxopropyl, 2-oxopentyl, 3-oxopentyl, 1-methyl-2-oxobutyl, 1-methyl-3-oxobutyl, 2-oxohexyl, 3-oxohexyl, 4-oxohexyl, 2-oxoheptyl, 3-oxoheptyl, 4-oxoheptyl, 4-oxoheptyl and the like.

For the purposes of the present invention, the expression "cycloalkyl" comprises unsubstituted monocyclic saturated hydrocarbon groups which generally have from 3 to 12 carbon ring members ($C_3$-$C_{12}$-cycloalkyl groups) such as cyclopropyl, cyclobutyl, cyclopentyl, cyclohexyl, cycloheptyl, cyclooctyl, cyclononyl, cyclodecyl, cycloundecyl or cyclododecyl, in particular $C_5$-$C_{12}$-cycloalkyl. The cycloalkyl radicals may have one or more (e.g. 1, 2, 3, 4, 5 or more than 5) substituents. Suitable substituents are generally selected from among alkyl, the substituents mentioned above for the alkyl groups, and also alkoxy. In the case of halogen, the hydrogen atoms of the substituted cycloalkyl groups may be partially or fully substituted by halogen.

Examples of unsubstituted and substituted cycloalkyl groups are cyclopentyl, 2- and 3-methylcyclopentyl, 2- and 3-ethylcyclopentyl, chloropentyl, dichloropentyl, dimethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, chlorohexyl, dimethylcyclohexyl, diethylcyclohexyl, methoxycyclohexyl, dimethoxycyclohexyl, diethoxycyclohexyl, butoxycyclohexyl, methylthiocyclohexyl, chlorocyclohexyl, dichlorocyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl, partially fluorinated cycloalkyl and perfluorinated cycloalkyl of the formula $C_nF_{2(n-a)-(1-b)}H_{2a-b}$ Where n=5 to 12, 0<=a<=n and b=0 or 1.

The expression "cycloalkyl" also includes in its definition the expression "$C_5$-$C_6$-cycloalkyl".

Ionic liquids for the purposes of the present specification denote organic salts which are liquid even at temperatures below 250° C. The ionic liquids preferably possess a melting point of less than 220° C., more preferably less than 200° C., in particular less than 150° C.

Ionic liquids which are present in the liquid aggregate state even at room temperature are described for example by K. N. Marsh et al., Fluid Phase Equilibria 219 (2004), 93-98 and J. G. Huddleston et al., Green Chemistry 2001, 3, 156-164.

The ionic liquid contains both cations and anions. Within the ionic liquid, a proton or an alkyl radical may be transferred from the cation to the anion, resulting in two neutral molecules. In the ionic liquid used in accordance with the invention, there is generally an equilibrium between anions, cations, and neutral molecules formed from them.

The ionic liquids used in accordance with the invention have polyatomic, i.e. multiatomic anions, having two or more than two atoms.

The expression "alkoxy" is an alkyl group bonded via an oxygen atom. Examples of alkoxy are: methoxy, ethoxy, n-propoxy, 1-methylethoxy, butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethyl propoxy, 1-ethyl-1-methylpropoxy or 1-ethyl-2-methylpropoxy, hexoxy and also $R^A O$—$(CH_2CH_2CH_2CH_2O)_n$—$CH_2CH_2CH_2CH_2O$— where $R^A$ is hydrogen or $C_1$-$C_4$-alkyl, preferably hydrogen, methyl or ethyl, and n is from 0 to 10, preferably from 0 to 3.

The expression "alkoxy" also includes in its definition the expression "$C_1$-$C_6$-alkoxy".

Alkylsulfinyl is an alkyl group bonded via an $S(=O)$ group.

Alkylsulfonyl is an alkyl group bonded via an $S(=O)_2$ group.

Alkyl radicals substituted by aryl ("arylalkyl") have at least one unsubstituted or substituted aryl groups as defined below. Suitable substituents on the aryl group are those stated below. The alkyl group in "arylalkyl" may carry at least one further substituent as defined above and/or may be interrupted by one or more nonadjacent heteroatoms or heteroatom—comprising groups selected from among —O—, —S—, —$NR^a$—, and/or —$SO_2$—. Arylalkyl is preferably phenyl-$C_1$-$C_{10}$-alkyl, particularly preferably phenyl-$C_1$-$C_4$-alkyl, for example benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)-eth-1-yl, 1-(phenmethyl)-1-(methyl)-eth-1-yl or -(phenmethyl)-1-(methyl)-prop-1-yl; preferably benzyl and 2-phenethyl.

For the purposes of the present invention, the expression "alkenyl" comprises unsubstituted straight-chain and branched alkenyl groups which, depending on the length of the chain, may have one or more double bonds (e.g. 1, 2, 3, 4 or more than 4). Preference is given to $C_2$-$C_{18}$-, particularly preferably $C_2$-$C_{10}$-alkenyl groups. Alkenyl is then, for example, ethenyl (vinyl), 1-propenyl, 2-propenyl, 1-methylethenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl and the like.

The alkenyl groups may have one or more (e.g. 1, 2, 3, 4, 5 or more than 5) substituents. Suitable substituents are, for example, selected from among =O, cycloalkyl, cycloalkyloxy, polycyclyl, heterocycloalkyl, aryl, hetaryl, halogen, alkylsulfinyl, alkylsulfonyl, $NE^3E^4$, nitro and cyano, where $E^3$ and $E^4$ are each, independently of one another, hydrogen, alkyl, cycloalkyl, heterocycloalkyl, aryl or hetaryl.

In the alkenyl radicals the carbon chain may be interrupted by one or more nonadjacent heteroatoms or heteroatom-comprising groups which are preferably selected from among —O—, —S—, —$NR^a$— and/or —$SO_2$—.

The expression "alkenyl" also includes in its definition the expressions "$C_1$-$C_{10}$-alkenyl" and "$C_1$-$C_6$-alkenyl".

Cycloalkyloxy is a cycloalkyl group as defined above which is bonded via oxygen.

The expression "cycloalkenyl" comprises unsubstituted and monounsaturated or diunsaturated hydrocarbon groups having from 3 to 5, up to 8 to up to 12, preferably from 5 to 12, carbon ring members, e.g. cyclopent-1-en-1-yl, cyclopent-2-en-1-yl, cyclopent-3-en-1-yl, cyclohex-1-en-1-yl, cyclohex-2-en-1-yl, cyclohex-3-en-1-yl, cyclohexa-2,5-dien-1-yl and the like. Suitable substituents are those mentioned above for cycloalkyl.

Cycloalkenyloxy is a cycloalkenyl group as defined above which is bonded via oxygen.

For the purposes of the present invention, the expression "polycyclyl" comprises in the broadest sense compounds which comprise at least two rings, regardless of how these rings are linked. They can be carbocyclic and/or heterocyclic rings. The rings can be saturated or unsaturated. The rings can be linked via a single or double bond ("multinuclear compounds"), joined by fusion ("fused ring systems") or bridged ("bridged ring systems", "cage compounds"). Preferred polycyclic compounds are bridged ring systems and fused ring systems. Fused ring systems can be aromatic, hydroaromatic and cyclic compounds linked by fusion (fused-on). Fused ring systems comprise two, three or more than three rings. Depending on the way in which the rings are linked, a distinction is made in the case of fused ring systems between ortho-fusion, i.e. each ring shares an edge or two atoms with each neighboring ring, and peri-fusion in which one carbon atom belongs to more than two rings. Among fused ring systems, preference is given to ortho-fused ring systems. For the purposes of the present invention, bridged ring systems include ones which are neither included among multinuclear ring systems nor among fused ring systems and in which at least two ring atoms belong to at least two different rings. In the case of bridged ring systems, a distinction is made, according to the number of ring-opening reactions which are formally required to obtain an open-chain compound, between bicyclo, tricyclo and tetracyclo compounds, etc., which comprise two, three, four, etc., rings. The expression "bicycloalkyl" comprises bicyclic hydrocarbon radicals having preferably from 5 to 10 carbon atoms, e.g. bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl, bicyclo[4.4.0]decyl and the like. The expression "bicycloalkenyl" comprises monounsaturated, bicyclic hydrocarbon radicals having preferably from 5 to 10 carbon atoms, e.g. bicyclo[2.2.1]hept-2-en-1-yl.

For the purposes of the present invention, the expression "aryl" comprises monocyclic or polycyclic aromatic hydrocarbon radicals. Aryl is generally hydrocarbon radicals having from 6 to 10, up to 14, up to 18, preferably from 6 to 10, carbon ring members. Aryl is preferably unsubstituted or substituted phenyl, naphthyl, anthracenyl, phenanthrenyl, naphthacenyl, chrysenyl, pyrenyl, etc., and particularly preferably phenyl or naphthyl. The aryl groups can, depending on the number and size of ring systems in them, have one or more (e.g. 1, 2, 3, 4, 5 or more than 5) substituents. These are preferably selected independently of one another from among alkyl, alkoxy, cycloalkyl, cycloalkyloxy, heterocycloalkyl, aryl, aryloxy, hetaryl, halogen, alkylsulfinyl, alkylsulfonyl, $NE^5E^6$, nitro and cyano, where $E^5$ and $E^6$ are each, independently of one another, hydrogen, alkyl, cycloalkyl, cycloalkyloxy, polycyclylyl, polycyclyloxy, heterocycloalkyl, aryl, aryloxy or hetaryl. Aryl is particularly preferably phenyl, which if it is substituted can generally bear 1, 2, 3, 4 or 5, preferably 1, 2 or 3, substituents.

Aryl which bears one or more radicals is, for example, 2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert-butylphenyl, 2,4-, 2,5-, 3,5- and 2,6-di-tert-butylphenyl, 2,4,6-tri-tert-butylphenyl and 2-, 3-, 4-dodecylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxy-phenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl, 2-, 3- and 4-butoxyphenyl, 2-, 3-, 4-hexyloxy-phenyl; 2-, 3-, 4-chlorophenyl, 2,4-, 2,5-, 3,5- and 2,6-dichlorophenyl, trichlorophenyl, 2-, 3-, 4-fluorophenyl, 2,4-, 2,5-, 3,5- and 2,6-difluorophenyl, trifluorophenyl, for example 2,4,6-trifluorophenyl, tetrafluorophenyl, pentafluorophenyl, 2-, 3- and 4-cyanophenyl; 2-nitrophenyl, 4-nitrophenyl, 2,4-dinitrophenyl, 2,6-dinitrophenyl; 4-dimethylaminophenyl; 4-acetylphenyl; methoxyethylphenyl, ethoxymethylphenyl; methylthiophenyl, isopropylthiophenyl or tert-butylthiophenyl; methylnaphthyl; isopropylnaphthyl or ethoxynaphthyl. Examples of substituted aryl in which two substituents bonded to adjacent carbon atoms of the aryl ring form a fused ring or fused ring system are indenyl and fluorenyl.

For the purposes of the present invention, the expression "aryloxy" refers to aryl bonded via an oxygen atom.

For the purposes of the present invention, the expression "heterocycloalkyl" comprises unsubstituted, nonaromatic, unsaturated or fully saturated, cycloaliphatic groups which generally have from 5 to 8 ring atoms, preferably 5 or 6 ring atoms, and in which 1, 2 or 3 of the ring carbons have been replaced by heteroatoms selected from among oxygen, nitrogen, sulfur and a group $—NR^a—$. Heterocycloalkyl groups can be substituted by one or more, for example 1, 2, 3, 4, 5 or 6, $C_1$-$C_6$-alkyl groups. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothienyl, dihydrothienyl, tetrahydrofuranyl, dihydrofuranyl, tetrahydropyranyl, 1,2-oxazolin-5-yl, 1,3-oxazolin-2-yl and dioxanyl. Nitrogen-comprising heterocycloalkyl can in principle be bonded either via a carbon atom or via a nitrogen atom.

For the purposes of the present invention, the expression "heteroaryl (hetaryl)" comprises unsubstituted, heteroaromatic, monocyclic or polycyclic groups which generally have from 5 to 14 ring atoms, preferably 5 or 6 ring atoms, and in which 1, 2 or 3 of the ring carbons have been replaced by one, two, three or four heteroatoms selected from among O, N, $—NR^a—$ and S. Examples of heteroaryl groups include furyl, thienyl, oxazolyl, isoxazolyl, thiazolyl, isothiazolyl, benzofuranyl, benzthiazolyl, benzimidazolyl, pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl. The heterocycloaromatic groups can generally bear 1, 2 or 3 substituents. The substituents are generally selected from among $C_1$-$C_6$-alkyl, $C_1$-$C_6$-alkoxy, hydroxy, carboxy, halogen and cyano.

5- to 7-membered nitrogen-comprising heterocycloalkyl or heteroaryl radicals which optionally comprise further heteroatoms are, for example, pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isooxazolyl, thiazolyl, isothiazolyl, indolyl, quinolinyl, isoquinolinyl or quinaldinyl.

Halogen is fluorine, chlorine, bromine or iodine.

For the purposes of the present invention, the expression "acyl" refers to alkanoyl, hetaroyl or aroyl groups generally having from 1 to 11, preferably from 2 to 8, carbon atoms, for example the formyl, acetyl, propanoyl, butanoyl, pentanoyl, hexanoyl, heptanoyl, 2-ethylhexanoyl, 2-propylheptanoyl, benzoyl or naphthoyl group.

The radicals $E^1$ and $E^2$, $E^3$ and $E^4$, $E^5$ and $E^6$ are selected independently of one another from among hydrogen, alkyl, cycloalkyl and aryl. The groups $NE^1E^2$, $NE^3E^4$ and $NE^5E^6$ are preferably N,N-dimethylamino, N,N-diethylamino, N,N-dipropylamino, N,N-diiso-propylamino, N,N-di-n-butylamino, N,N-di-tert-butylamino, N,N-dicyclohexylamino or N,N-diphenylamino.

The anion $[Y]^{m-}$ of the at least one ionic liquid of the general formula (I), used in the process of the invention, is an m-valent multiatomic anion where m has the value 1, 2, 3 or 4.

The anion $[Y]^{m-}$ of the at least one ionic liquid is selected from:

the group of pseudohalides and halogen-comprising compounds of the formulae:

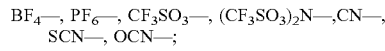

the group of sulfonates of the general formula:

the group of phosphites of the general formulae:

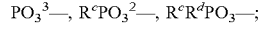

the group of phosphonites and phosphinites of the general formulae:

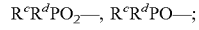

the group of borates of the general formulae:

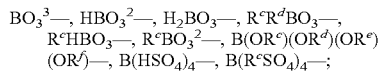

the group of boronates of the general formulae:

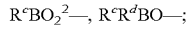

the group of silicates and silicic esters of the general formulae:

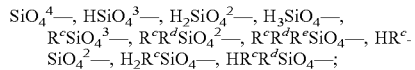

the group of alkyl- and arylsilanolates of the general formulae:

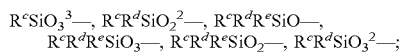

the group of the carboximides, bis(sulfonyl)imides and sulfonylimides of the general formulae

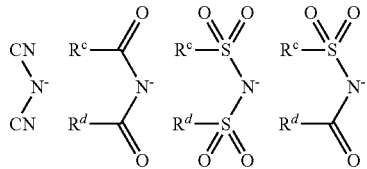

the group of methides of the general formula:

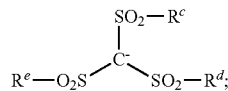

the group of hydrogensulfides, polysulfides and hydrogenpolysulfides of the general formulae:

$[S_v]^{2-}$, $[HS_v]^{-}$, where v is a positive integer from 2 to 10, where the radicals $R^c$, $R^d$, $R^e$ and $R^f$ independently of one another are selected from hydrogen, unsubstituted or substituted alkyl, cycloalkyl, heterocycloalkyl, aryl, heteroaryl, where in anions which have two or more radicals $R^c$ to $R^f$, it is also possible for two of these radicals in each case, together with the part of the anions to which they are bonded, to be at least one saturated, unsaturated or aromatic ring or ring system having 1 to 12 carbon atoms, it being possible for the ring or ring system to contain 1 to 5 nonadjacent heteroatoms or heteroatom-containing groups, preferably selected from oxygen, nitrogen, sulfur and $NR^a$, and for the ring or ring system to be unsubstituted or substituted.

Preferred anions are selected from the group of pseudohalides and halogen-comprising compounds, the group of sulfonates, and the group of phosphates.

Particularly preferred anions are $BF_4-$, $PF_6-$, $CF_3SO_3-$, $SCN-$, $PO_3^{3-}$, $R^cPO_3^{2-}$ and $R^cSO_3-$, where $R^c$ has the definition stated above.

In one preferred embodiment of the process of the invention, the at least one ionic liquid is selected from salts of the general formula (Ia),

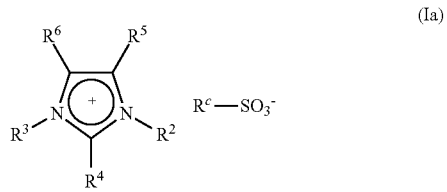

(Ia)

in which
radicals $R^2$ and $R^3$, independently of one another, are hydrogen, unsubstituted or substituted alkyl, alkenyl, cycloalkyl, cycloalkenyl, aryl or heteroaryl,
radicals $R^4$, $R^5$ and $R^6$, independently of one another, are hydrogen, unsubstituted or substituted alkyl, alkenyl, cycloalkyl, cycloalkenyl, heterocycloalkyl, aryl, heteroaryl or alkoxy,
and
$R^c$ is alkyl, cycloalkyl or aryl, where aryl may be substituted by 1, 2 or 3 alkyl radicals.

In one particularly preferred embodiment of the process of the invention, the at least one ionic liquid is selected from salts of the general formula (Ia) in which
radicals $R^2$ and $R^3$ independently of one another are hydrogen, unsubstituted $C_1$-$C_6$-alkyl, unsubstituted $C_2$-$C_6$-alkenyl, unsubstituted $C_5$-$C_6$-cycloalkyl, $C_6$-$C_{10}$-aryl or heteroaryl having 5 to 6 ring atoms, it also being possible for the 2 last-mentioned radicals to have 1, 2 or 3 substituents selected from $C_1$-$C_6$-alkyl, $C_1$-$C_6$-alkoxy or halogen,
radicals $R^4$, $R^5$ and $R^6$ independently of one another are hydrogen, unsubstituted $C_1$-$C_6$-alkyl, unsubstituted $C_5$-$C_6$-cycloalkyl or benzyl, it also being possible for benzyl to have 1, 2 or 3 substituents selected from $C_1$-$C_6$-alkyl, $C_1$-$C_6$-alkoxy or halogen,
and
$R^c$ is unsubstituted $C_1$-$C_6$-alkyl, unsubstituted $C_5$-$C_6$-cycloalkyl or aryl, it being possible for aryl to be substituted by 1, 2 or 3 $C_1$-$C_6$-alkyl radicals.

In the compounds of the general formula (Ia), the radicals $R^2$ and $R^3$ independently of one another are especially hydrogen or unsubstituted $C_1$-$C_6$-alkyl and the radicals $R^4$, $R^5$, and $R^6$ are especially hydrogen.

Suitable ionic liquids for use in the process of the invention are available commercially, for example under the brand name Basionic® from BASF SE. Examples of those advantageous for use in the process of the invention are as follows: 1-ethyl-3-methylimidazolium methanesulfonate (EMIM $CH_3SO_3$, Basionic ST 35), 1-butyl-3-methylimidazolium methanesulfonate (BMIM $CH_3SO_3$, Basionic ST 78), 1-ethyl-3-methylimidazolium thiocyanate (BASIONIC™ VS 01) or 1-butyl-3-methylimidazolium thiocyanate (BASIONIC™ VS 02).

Particularly suitable ionic liquids for use in the process of the invention are, for example, 1-ethyl-3-methylimidazolium methanesulfonate (EMIM $CH_3SO_3$, Basionic ST 35) and 1-butyl-3-methylimidazolium methanesulfonate (BMIM $CH_3SO_3$, Basionic ST 78).

In one specific embodiment, the anion of the at least one ionic liquid used in the process of the invention corresponds to the deprotonated form of the organic sulfonic acid used as catalyst. If, for example, methanesulfonic acid is the catalyst used, the anion of the ionic liquid used is methylsulfonate.

Generally speaking, the reaction of the at least one carboxylic acid and/or of the at least one carboxylic anhydride and of the at least one alcohol $R^1$—OH is carried out in at least one reactor.

If the reaction is carried out in a plurality of reactors, the reactors are preferably arranged in series. The process of the invention can be carried out batchwise or continuously, but is preferably carried out continuously.

The reactors can be any desired reactors suitable for the conduct of liquid-phase chemical reactions.

Suitable reactors are non-backmixing reactors, for example tubular reactors or holding containers provided with internals, but preferably backmixing reactors, such as stirred tanks, loop reactors, or jet loop reactors. However, it is also possible to use combinations of successive backmixing reactors and non-backmixing reactors.

It is also optionally possible to combine a plurality of reactors in a multistage apparatus. These reactors are by way of example loop reactors with internal perforated plates, cascaded containers, tubular reactors with intermediate feed, or stirred columns.

Stirred-tank reactors are preferably used. The stirred-tank reactors are mostly composed of metallic materials, preference being given here to stainless steel. It is preferable that a stirrer or a circulating pump is used for vigorous mixing of the reaction mixture.

In one preferred embodiment, the process of the invention is carried out in a single stirred tank. In another preferred embodiment, the process of the invention is carried out in at least two stirred tanks connected to one another in the form of a cascade.

Specifically in the case of continuous conduct of the process, it can be advantageous for maximum conversion to connect a plurality of reactors in the form of a cascade. The reaction mixture passes through the individual reactors in succession, and the outflow from the first reactor here is introduced into the second reactor, the outflow from the second reactor is introduced into the third reactor, etc. The cascade can by way of example comprise from 2 to 10 reactors, a preferred number of reactors here being 2, 3, 4 or 5.

In the case of batchwise conduct of the process, carboxylic acid and/or carboxylic anhydride and alcohol $R^1$—OH and the ionic liquid and the catalyst can be charged simultaneously or in succession to the reactor. The catalyst can be introduced in pure form or as solution, preferably dissolved in one of the starting materials and/or the ionic liquid, at the start or only after the reaction temperature has been reached. Carboxylic anhydrides often react with alcohols autocatalytically, i.e. without catalysis, to give the corresponding ester acids (hemiesters), an example being phthalic anhydride giving the phthalic monoester. A catalyst is therefore often required only after the first reaction step. On account of the solubilizing qualities it is generally advantageous to add the ionic liquid at the start of the reaction.

In the case of continuous conduct of the process, streams of the starting materials, the ionic liquid and of the catalyst are introduced into the reactor or, if a reactor cascade is used, preferably into the first reactor of the cascade. The residence time in the reactor or in the individual reactors here is determined by the volume of the reactors and the flow rate of the starting materials.

In a preferred embodiment, the process of the invention takes place with introduction, to the reaction system, of a gas that is inert under the reaction conditions. To this end, the inert gas can be passed into the gas space of the reaction system or into the liquid reaction mixture. The introduction of the inert gas into the reaction system preferably takes place in a manner that creates a large area for interchange between the liquid reaction mixture and the inert gas. The treatment with the inert gas during the reaction has a stripping effect and completes the removal of the water of reaction. It is moreover possible to introduce energy into the reaction system by introducing a heated inert gas. In this embodiment, the introduction of energy by way of the reactor jacket can be reduced accordingly. It is thus advantageously possible to reduce any overheating of the reaction mixture in the vicinity of the reactor jacket, and to reduce the formation of byproducts.

In a particularly preferred embodiment, the inert gas is introduced into the boiling reaction mixture below the liquid surface in such a way that it bubbles through the reaction mixture. The pressure of the inert gas must be sufficiently high to overcome the hydrostatic pressure of the reaction mixture above the inert gas feed. By way of example, it is possible to introduce the inert gas from 20 to 50 cm below the liquid surface of the reaction mixture.

The inert gas can be fed into the system by way of any desired suitable apparatuses. Among these are by way of example nozzles for gas-supply lances. The nozzles can be on the base of the reactor or in the vicinity of the base. To this end, the nozzles can be designed as apertures of a hollow chamber surrounding the reactor. A possible alternative use is immersed nozzles with suitable supply lines. By way of example, there can be a plurality of nozzles arranged in the form of a ring. The nozzles can point upward or downward. The nozzles preferably point obliquely downward.

It is preferable that the reaction mixture is mixed in order to bring about an interchange of reaction mixture in the reactor region below the feed of the inert gas with reaction mixture in the reactor region above the feed of the inert gas. By way of example, stirrers or a circulating pump are suitable for the mixing process. In one specific variant, what is known as a gas-introducing stirrer is used for the introduction of the inert gas and for the mixing of the reaction mixture.

If the process of the invention is carried out in at least two stirred tanks connected to one another in the form of a cascade, it is preferable that the inert gas passes through all of the reactors of the cascade. If more than one reactor is treated with the inert gas, this can be conducted in parallel to the individual reactors, or the inert gas can pass through a plurality of reactors in succession. It is also possible to design combinations in which fresh inert gas bubbles through two or more reactors, and the vapor comprising the inert gas is passed from at least one of the reactors through at least one further reactor.

By way of example, fresh inert gas can be introduced into the final reactor in the direction of flow, and in a cascade of n reactors, the vapor comprising the inert gas can be collected from the nth reactor and introduced in the form of vapor into the reaction mixture in reactor (n−1, etc.).

The esterification reaction takes place according to the invention in the presence of an inert gas. The expression "inert gas" means a gas which, under the prevailing process conditions, does not enter into any reactions with the starting materials, reagents, or solvents involved in the reaction, or with the resultant products. Examples of suitable inert gases are nitrogen, helium, argon etc. It is preferable to use nitrogen as inert gas.

According to the invention, the process takes place with distillative removal of at least one portion of the water formed during the reaction, in the form of an azeotropic mixture with the alcohol $R^1$—OH used, which is then at least to some extent returned to the reaction system. To this end, a vapor is removed from the reaction system and is condensed, the condensate is separated into an aqueous phase and an alcohol phase, and the alcohol phase is at least to some extent returned to the reaction system. "Return to the reaction system" means that the alcohol phase is passed into any desired at least one reactor of the reaction system.

Any of the suitable condensers can be used for the condensation or partial condensation of the vapor. These can be cooled by any desired coolants. Preference is given to condensers with air cooling and/or water cooling, particular preference being given here to air cooling.

The resultant condensate is subjected to phase separation to give an aqueous phase and an organic phase. For this, the condensate is usually passed into a phase separator (decanter) where mechanical settling causes it to break down into two phases which can be extracted separately. The aqueous phase is removed and can, optionally after treatment, be discarded or used as stripping water in the post-treatment of the ester.

The vapor from the individual reactors of a cascade can be combined, and the resultant combined material can be condensed. It is optionally possible in each case to combine a plurality of reactors of the cascade to give a subunit, in which case then each subunit has a condenser coupled thereto. There is also moreover the possibility of coupling each reactor of the cascade to a condenser.

The alcohol phase to be returned can be passed into any desired reactor of a cascade, or can be divided over a plurality of reactors of the cascade. However, it is preferable that the alcohol phase to be returned is not passed into the final reactor of the cascade. It is preferable that the alcohol phase to be returned is passed exclusively or mainly into the first reactor of the cascade.

There are various possibilities for the return of the alcohol phase into the reaction system. In one possibility, the organic phase is, optionally after heating, pumped into the liquid reaction mixture.

For thermal optimization of the process, the alcohol phase can be returned by way of a column (known as return-alcohol column) into the reaction system. In said return-alcohol column, the returned alcohol phase is conducted in counterflow to at least a portion of the vapor. The alcohol phase is advantageously introduced into the return-alcohol column at the top or in the upper region. The outflow of condensate from the return-alcohol column passes back into the reaction system. When a reactor cascade is used, the outflow of condensate from the return-alcohol column is preferably introduced into the first reactor. The return of the alcohol phase by way of the return-alcohol column has the advantage that the returned alcohol phase is preheated and is freed from traces of water which have remained in the organic phase after phase separation or which are dissolved in the organic phase in accordance with their thermodynamic solubility. The return-alcohol column can by way of example be a plate column, packed column, or filled column. A small number of theoretical plates is generally sufficient. By way of example, a suitable column has from 2 to 10 theoretical plates. When a reactor cascade is used, it is preferable that the vapor leaves at least the first reactor by way of the return-alcohol column. One or more, or all of the, further reactors can likewise have a vapor outlet to the return-alcohol column.

The alcohol $R^1$—OH is preferably used in a stoichiometric excess with respect to the carboxy groups. It is assumed here that a carboxylic anhydride has two carboxy groups requiring esterification. It is particularly preferable that the alcohol $R^1$—OH is used in a 1 to 100% molar excess, in particular in a 5 to 50% molar excess, specifically in a 7 to 15% molar excess.

The amount preferably used of the catalyst is from 0.5 to 5 mol %, particularly from 1 to 2 mol %, based on the molar amount of carboxy groups.

It is preferable that the esterification catalyst is selected from methanesulfonic acid and toluenesulfonic acid. In particular, methanesulfonic acid is used as esterification catalyst. The catalyst can be used in the form of pure substance or in the form of an aqueous solution.

For the purposes of the present invention, the expression "total chlorine content" means the sum of the content of free chlorine and the content of chlorine bonded in organic or inorganic form.

The methanesulfonic acid used preferably has a total chlorine content of at most 20 ppm, preferably at most 5 ppm, in particular at most 1 ppm.

The methanesulfonic acid used preferably has a sulfate content of at most 50 ppm, preferably at most 20 ppm.

A particularly suitable pure methanesulfonic acid is obtainable by the process described in WO 0050351. This type of pure MSA is obtainable commercially as Lutropur® from BASF SE, either in the form of 70% aqueous solution (Lutropur® MSA) or in the form of anhydrous MSA (Lutropur® MSA100).

The esterification reaction is preferably carried out in the temperature range from 60 to 250° C., in particular from 120 to 240° C.

The ideal temperatures depend on the starting materials, on the progress of the reaction, and on the catalyst concentration. They can easily be determined for any individual case by experiments. In order to remove the water of reaction it is necessary that the alcohol can be removed by distillation from the reaction mixture. The desired temperature or the desired temperature range can be adjusted through the pressure in the reactor. In the case of low-boiling-point alcohols it is therefore possible to carry out the reaction at superatmospheric pressure or ambient pressure, and in the case of higher-boiling-point alcohols it is therefore possible to carry out the reaction at reduced pressure.

If the esterification reaction uses a cascade made of a plurality of reactors, it is possible that all of the reactors of a cascade are operated at the same temperature. However, it is generally preferable to increase the temperature continuously from the first to the final reactor of a cascade, the temperature at which a reactor is operated being the same as or higher than that of the reactor situated upstream in the direction of flow of the reaction mixture. All of the reactors can advantageously be operated at in essence the same pressure.

The esterification reaction preferably takes place at ambient pressure or at reduced pressure. It is preferable to carry out the esterification reaction at a pressure of from 0.001 to 2.0 bar, particularly from 0.01 to 1.1 bar.

The esterification reaction can be carried out in the absence of any external solvent or in the presence of an organic solvent. It is preferable to carry out the esterification reaction in the absence of any external solvent.

If the esterification reaction is carried out in the presence of an external solvent, this is preferably an organic solvent that is inert under the reaction conditions. Among these are by way of example aliphatic hydrocarbons, halogenated aliphatic hydrocarbons, aromatic and substituted aromatic hydrocarbons, and ethers. It is preferable that the solvent is selected from pentane, hexane, heptane, ligroin, petroleum ether, cyclohexane, dichloromethane, trichloromethane, tetrachloromethane, benzene, toluene, xylene, chlorobenzene, dichlorobenzenes, dibutyl ether, THF, dioxane, N,N-dimethylformamide, dimethyl sulfoxide, polyethers, for example polyalkylene glycols, such as polyethylene glycols (PEG), polyalkylene glycol mono-($C_1$-$C_4$)-alkyl ethers, such as polyethylene glycol monomethyl ether (MPEG), polyalkylene glycol di-($C_1$-$C_4$)-alkyl ethers, such as polyethylene glycol dimethyl ether, having a boiling point of above 200° C., and mixtures thereof.

Generally speaking, the fraction of the ionic liquid in the reaction mixture is 1 to 50% by weight, preferably 2 to 45% by weight, in particular 5 to 40% by weight, based on the total weight of the reaction mixture.

Once the reaction has ended, the reaction mixture present in the liquid phase consists customarily of two phases: an organic phase, which contains the desired ester and excess alcohol, and an ionic fraction, which contains the ionic liquid, the catalyst and/or derivatives thereof, and also small amounts of ester carboxylic acid(s) and/or of unreacted carboxylic acid.

Generally speaking, once the reaction has ended, the ionic fraction, which contains the at least one catalyst and also optionally unreacted carboxylic acid and/or unreacted carboxylic anhydride, is removed from the reaction mixture and used again for further esterification reactions.

The separation of the reaction mixture into the organic phase and the ionic fraction takes place customarily via a process of self-separation (phase separation). For this purpose, the reaction mixture is passed into a phase separator (decanter), where it parts by mechanical settling into two phases (the organic product phase and the ionic fraction), which can be taken off separately.

If separation cannot be achieved, or achieved completely, by means of self-separation (phase separation), the separation can be accomplished by extraction as well or instead. In that case, the reaction mixture is extracted in general using a solvent which is a very good solvent for the ester compound but has little miscibility or none at all with the ionic liquid. Alternatively, for the extractive separation of the reaction mixture, it is also possible to use a solvent which is a very good solvent for the ionic liquid but has little miscibility, or none at all, with the ester compound.

Solvents suitable for the extraction that are of little miscibility or none at all with the ionic liquid are selected, for example, from aliphatic hydrocarbons, such as pentane, hexane, heptane, ligroin, petroleum ether, cyclopentane or cyclohexane, halogenated aliphatic hydrocarbons, such as dichloromethane, trichloromethane, carbon tetrachloride or 1,2-dichloroethane, aromatic hydrocarbons, such as benzene, toluene, xylene, halogenated aromatic hydrocarbons, such as chlorobenzene, dichlorobenzenes, ethers, such as diethyl ether, methyl tert-butyl ether, dibutyl ether, tetrahydrofuran or dioxane, and also $C_1$-$C_4$-alkylnitriles, such as acetonitrile or propionitrile, and the like.

Extractive separation of the reaction mixture is accomplished preferably using a solvent which is a very good solvent for the ionic liquid but has little miscibility or none at all with the ester compound. Solvents suitable for this purpose are selected for example from water and $C_1$-$C_4$-alcohols, such as methanol, ethanol or 2-propanol, especially water.

When separation has been accomplished, the ionic fraction, which contains the ionic liquid, the catalyst and/or derivatives thereof, and also small amounts of ester carboxylic acid(s) and/or of unreacted carboxylic acid, can be stored and used again for further reactions.

When separation has been accomplished, the organic phase, which contains the desired ester and excess alcohol, can be subjected to further steps of work-up and/or purification.

Generally speaking, for further work-up, the organic phase is washed with aqueous base, in order to remove and/or to neutralize any acidic compounds present in this phase. The excess alcohol is subsequently removed by distillation. The sequence of the process steps here can be varied. Most of the unreacted alcohol is removed here by distillation at atmospheric pressure or in vacuo. The final traces of the alcohol can by way of example be removed by steam distillation, in particular in the temperature range from 120 to 225° C. in vacuo. The removal of the alcohol can be a first or a final work-up step.

The neutralization of the acidic substances, such as carboxylic acids, ester carboxylic acids, or optionally the acidic catalysts, is achieved by adding bases, e.g. alkali metal carbonates and/or alkaline earth metal carbonates, alkali metal hydrogencarbonates, alkaline earth metal hydrogencarbonates, or alkali metal hydroxides or alkaline earth metal hydroxides. The neutralizing agent can be used in solid form or preferably in the form of solution, in particular in the form of aqueous solution. Aqueous sodium hydroxide solution is often used here at a concentration of from 0.1 to 30% by weight, preferably from 0.5 to 15% by weight, in particular from 1 to 10% by weight. The amount added of the neutralizing agent is from one to four times, in particular from one to two times, the stoichiometrically required amount determined by titration.

The distillation process also removes the ether, resulting as byproduct, of the alcohol $R^1$—OH used, to the extent that said ether is present. The amount of this ether comprised in the reaction mixtures obtained after the process of the invention is generally <2% by weight, preferably <1% by weight (determined by qualitative GC measurements on derivatized samples). The resultant ether can, if desired, be converted by acidic ether cleavage back to the alcohol $R^1$—OH.

The excess alcohol $R^1$—OH can be directly reused, or can be further purified, e.g. by means of distillation.

The resultant carboxylic ester is in essence free from solid contaminants. However, it can be subjected to filtration in order to remove any substances that may be present in suspension in the reactor.

Preferred alcohols $R^1$—OH are $C_5$-$C_{13}$-alkanols. The $C_5$-$C_{13}$-alkanols can be straight-chain or branched, or be composed of mixtures of straight-chain and branched $C_5$-$C_{13}$-alkanols. Among the preferred $C_5$-$C_{13}$-alkanols are by way of example n-pentanol, 2-methylbutanol, n-hexanol, n-heptanol, isoheptanol, n-octanol, isooctanol, 2-ethylhexanol, n-nonanol, isononanol, isodecanol, 2-propylheptanol, n-undecanol, isoundecanol, n-dodecanol, isododecanol, n-tridecanol, and isotridecanol, and also mixtures thereof. Particular preference is given to $C_7$-$C_{12}$-alkanols.

$C_7$-$C_{12}$-alkanols particularly preferred as alcohols $R^1$—OH can be straight-chain or branched or be composed of mixtures of straight-chain and branched $C_7$-$C_{12}$-alkanols. Among the particularly preferred $C_7$-$C_{12}$-alkanols are by way of example n-octanol, 2-ethylhexanol, n-nonanol, isononanol, isodecanol, 2-propylheptanol, n-undecanol, isoundecanol, and n-dodecanol, and also mixtures thereof. In particular, 2-ethylhexanol is used as alcohol in the process of the invention.

Preference is further given to use of $C_5$-$C_6$-cycloalkanols, and also of $C_5$-$C_{13}$-alkanols, as alcohols $R^1$—OH. The $C_5$-$C_6$-cycloalkanols are selected from cyclopentanol and cyclohexanol, and also mixtures thereof. Cyclohexanol is preferred. Substituted $C_5$-$C_6$-cycloalkanols can, as appropriate to their ring size, have one or more (e.g. 1, 2, 3, 4, or 5) $C_1$-$C_{10}$-alkyl substituents. Examples of $C_5$-$C_6$-cycloalkanols are 2- and 3-methylcyclopentanol, 2- and 3-ethylcyclopentanol, 2-, 3- and 4-methylcyclohexanol, 2-, 3-, and 4-ethylcyclohexanol, 2-, 3-, and 4-propylcyclohexanol, 2-, 3-, and 4-isopropylcyclohexanol, 2-, 3-, and 4-butylcyclohexanol, 2-, 3-, and 4-sec-butylcyclohexanol, and 2-, 3-, and 4-tert-butylcyclohexanol.

Particularly preferred $C_7$-$C_{12}$-alkanols are defined in more detail below.

Heptanol

The heptanols used in the process of the invention can be straight-chain or branched or can be composed of mixtures of straight-chain and branched heptanols. It is preferable to use mixtures of branched heptanols, also known as isoheptanol, which are produced via rhodium- or preferably cobalt-catalyzed hydroformylation of propene dimer, obtainable by way of example by the Dimersol® process, and subsequent hydrogenation of the resultant isoheptanals to give an isoheptanol mixture. Because of the process used for its production, the resultant isoheptanol mixture is composed of a plurality of isomers. Substantially straight-chain heptanols can be obtained via rhodium- or preferably cobalt-catalyzed hydroformylation of 1-hexene and subsequent hydrogenation of the resultant n-heptanal to give n-heptanol. The hydroformylation of 1-hexene or of propene dimer can be achieved by methods known per se: compounds used as catalyst in hydroformylation with rhodium catalysts homogeneously dissolved in the reaction medium can be not only uncomplexed rhodium carbonyl compounds which are formed in situ under the conditions of the hydroformylation reaction within the hydroformylation reaction mixture on exposure to synthesis gas, e.g. from rhodium salts, but also complex rhodium carbonyl compounds, in particular complexes with organic phosphines, such as triphenylphosphine, or with organophosphites, preferably chelating biphosphites, as described by way of example in U.S. Pat. No. 5,288,918. Compounds used in the cobalt-catalyzed hydroformylation of these olefins are generally cobalt carbonyl compounds which are homogeneously soluble in the reaction mixture and which are formed in situ from cobalt salts under the conditions of the hydroformylation reaction on exposure to synthesis gas. If the cobalt-catalyzed hydroformylation is carried out in the presence of trialkyl- or triarylphosphines, the desired heptanols are formed directly as hydroformylation product, and there is therefore then no need for further hydrogenation of the aldehyde function.

Examples of suitable processes for the cobalt-catalyzed hydroformylation of 1-hexene or of the hexene isomer mixtures are the established industrial processes explained on pages 162-168 of Falbe, New Syntheses with Carbon Monoxide, Springer, Berlin, 1980, an example being the Ruhrchemie process, the BASF process, the Kuhlmann process, or the Shell process. Whereas the Ruhrchemie, BASF, and Kuhlmann process operate with non-ligand-modified cobalt carbonyl compounds as catalysts and thus give hexanal mixtures, the Shell process (DE-A 1593368) uses, as catalyst, phosphine- or phosphite-ligand-modified cobalt carbonyl compounds which lead directly to the hexanol mixtures because they also have high hydrogenation activity. DE-A 2139630, DE-A 2244373, DE-A 2404855, and WO 01014297 provide detailed descriptions of advantageous embodiments for the conduct of the hydroformylation with non-ligand-modified cobalt carbonyl complexes.

The rhodium-catalyzed hydroformylation of 1-hexene or of the hexene isomer mixtures can use the established industrial low-pressure rhodium hydroformylation process with triphenylphosphine-ligand-modified rhodium carbonyl compounds, which is subject matter of U.S. Pat. No. 4,148,830. Non-ligand-modified rhodium carbonyl compounds can serve advantageously as catalyst for the rhodium-catalyzed hydroformylation of long-chain olefins, for example of the hexene isomer mixtures obtained by the processes described above; this differs from the low-pressure process in requiring a higher pressure of from 80 to 400 bar. The conduct of high-pressure rhodium hydroformylation processes of this type is described by way of example in EP-A 695734, EP-B 880494, and EP-B 1047655.

The isoheptanal mixtures obtained after hydroformylation of the hexene isomer mixtures are catalytically hydrogenated in a manner that is per se conventional to give isoheptanol mixtures. For this purpose it is preferable to use heterogeneous catalysts which comprise, as catalytically active component, metals and/or metal oxides of group VI to VIII, or else of transition group I, of the periodic table of the elements, in particular chromium, molybdenum, manganese, rhenium, iron, cobalt, nickel, and/or copper, optionally deposited on a support material, such as $Al_2O_3$, $SiO_2$ and/or $TiO_2$. Catalysts of this type are described by way of example in DE-A 3228881, DE-A 2628987, and DE-A 2445303. It is particularly advantageous to carry out the hydrogenation of the isoheptanals with an excess of hydrogen of from 1.5 to 20% above the stoichiometric amount of hydrogen needed for the hydrogenation of the isoheptanals, at temperatures of from 50 to 200° C., and at a hydrogen pressure of from 25 to 350 bar, and for avoidance of side-reactions to add, during the course of the hydrogenation, in accordance with DE-A 2628987, a small amount of water, advantageously in the form of an aqueous solution of an alkali metal hydroxide or alkali metal carbonate, in accordance with the teaching of WO 01087809.

Octanol

For many years, 2-ethylhexanol was the largest-production-quantity plasticizer alcohol, and it can be obtained through the aldol condensation of n-butyraldehyde to give 2-ethylhexanal and subsequent hydrogenation thereof to give 2-ethylhexanol (see Ullmann's Encyclopedia of Industrial Chemistry; $5^{th}$ edition, vol. A 10, pp. 137-140, VCH Verlagsgesellschaft GmbH, Weinheim 1987).

Substantially straight-chain octanols can be obtained via rhodium- or preferably cobalt-catalyzed hydroformylation of 1-heptene and subsequent hydrogenation of the resultant n-octanal to give n-octanol. The 1-heptene needed for this purpose can be obtained from the Fischer-Tropsch synthesis of hydrocarbons.

By virtue of the production route used for the alcohol isooctanol, it is not a unitary chemical compound, in contrast to 2-ethylhexanol or n-octanol, but instead is an isomer mixture of variously branched $C_8$-alcohols, for example of 2,3-dimethyl-1-hexanol, 3,5-dimethyl-1-hexanol, 4,5-dimethyl-1-hexanol, 3-methyl-1-heptanol, and 5-methyl-1-heptanol; these can be present in the isooctanol in various quantitative proportions which depend on the production conditions and production processes used. Isooctanol is usually produced via codimerization of propene with butenes, preferably n-butenes, and subsequent hydroformylation of the resultant mixture of heptene isomers. The octanal isomer mixture obtained in the hydroformylation can subsequently be hydrogenated to give the isooctanol in a manner that is conventional per se.

The codimerization of propene with butenes to give isomeric heptenes can advantageously be achieved with the aid of the homogeneously catalyzed Dimersol® process (Chauvin et al; Chem. Ind.; May 1974, pp. 375-378), which uses, as catalyst, a soluble nickel phosphine complex in the presence of an ethylaluminum chlorine compound, for example ethylaluminum dichloride. Examples of phosphine ligands that can be used for the nickel complex catalyst are tributylphosphine, triisopropyl-phosphine, tricyclohexyl-phosphine, and/or tribenzylphosphine. The reaction takes place at temperatures of from 0 to 80° C., and it is advantageous here to set a pressure at which the olefins are present in solution in the liquid reaction mixture (Cornils; Hermann: Applied Homogeneous Catalysis with Organometallic Compounds; $2^{nd}$ edition, vol. 1; pp. 254-259, Wiley-VCH, Weinheim 2002).

In an alternative to the Dimersol® process operated with nickel catalysts homogeneously dissolved in the reaction medium, the codimerization of propene with butenes can also be carried out with a heterogeneous NiO catalyst deposited on a support; heptene isomer distributions obtained here are similar to those obtained in the homogeneously catalyzed process. Catalysts of this type are by way of example used in what is known as the Octol® process (Hydrocarbon Processing, February 1986, pp. 31-33), and a specific heterogeneous nickel catalyst with good suitability for olefin dimerization or olefin codimerization is disclosed by way of example in WO 9514647.

Codimerization of propene with butenes can also use, instead of nickel-based catalysts, heterogeneous Brønsted-acid catalysts; heptenes obtained here are generally more highly branched than in the nickel-catalyzed processes. Examples of catalysts suitable for this purpose are solid phosphoric acid catalysts, e.g. phosphoric-acid-impregnated kieselguhr or diatomaceous earth, these being as utilized in the PolyGas® process for olefin dimerization or olefin oligomerization (Chitnis et al; Hydrocarbon Engineering 10, No. 6-June 2005). Brønsted-acid catalysts that have very good suitability for the codimerization of propene and butenes to give heptenes are zeolites, which are used in the EMOGAS® process, a further development based on the PolyGas® process.

The 1-heptene and the heptene isomer mixtures are converted to n-octanal and, respectively, octanal isomer mixtures by the known processes explained above in connection with the production of n-heptanal and heptanal isomer mixtures, by means of rhodium- or cobalt-catalyzed hydroformylation, preferably cobalt-catalyzed hydroformylation. These are then hydrogenated to give the corresponding octanols, for example by means of one of the catalysts mentioned above in connection with production of n-heptanol and of isoheptanol.

Nonanol

Substantially straight-chain nonanol can be obtained via rhodium- or preferably cobalt-catalyzed hydroformylation of 1-octene and subsequent hydrogenation of the resultant n-nonanal. The starting olefin 1-octene can be obtained by way of example by way of ethylene oligomerization by means of a nickel complex catalyst that is homogenously soluble in the reaction medium-1,4-butanediol-with, for example, diphenyl-phosphinoacetic acid or 2-diphenylphosphinobenzoic acid as ligand. This process is also known as the Shell Higher Olefins Process or SHOP process (see Weisermel, Arpe: Industrielle Organische Chemie [Industrial organic chemistry]; $5^{th}$ edition, p. 96; Wiley-VCH, Weinheim 1998).

The alcohol component isononanol used in the process of the invention is not a unitary chemical compound, but instead is a mixture of variously branched, isomeric $C_9$-alcohols which can have various degrees of branching, depending on the manner in which they were produced, and also in particular on the starting materials used. The isononanols are generally produced via dimerization of butenes to give isooctene mixtures, subsequent hydroformylation of the isooctene mixtures, and hydrogenation of the resultant isononanal mixtures to give isononanol mixtures, as explained in Ullmann's Encyclopedia of Industrial Chemistry, $5^{th}$ edition, vol. A1, pp. 291-292, VCH Verlagsgesellschaft GmbH, Weinheim 1995.

Isobutene, cis- and trans-2-butene, and also 1-butene, or a mixture of these butene isomers, can be used as starting material for the production of the isononanols. The dimerization of pure isobutene, mainly catalyzed by means of liquid Brønsted acids, e.g. sulfuric acid or phosphoric acid, or by means of solid Brønsted acids, e.g. phosphoric acid absorbed on kieselguhr, $SiO_2$, or $Al_2O_3$, as support material, or zeolites, mainly gives the highly branched compound 2,4,4-trimethylpentene, also termed diisobutylene, which gives highly branched isononanols after hydroformylation and hydrogenation of the aldehyde.

Preference is given to isononanols with a low degree of branching. Isononanol mixtures of this type with little branching are obtained from the linear butenes 1-butene, and cis- and/or trans-2-butene which optionally can also comprise relatively small amounts of isobutene, by way of the route described above involving butene dimerization, hydroformylation of the isooctene, and hydrogenation of the resultant isononanal mixtures. A preferred raw material is what is known as raffinate II, from the $C_4$ cut of a cracker, for example of a steam cracker, which is obtained after elimination of allenes, acetylenes, and dienes, in particular 1,3-butadiene, via partial hydrogenation thereof to give linear butenes, or removal thereof via extractive distillation, for example by means of N-methylpyrrolidone, and subsequent Brønsted-acid catalyzed removal of the isobutene comprised therein via reaction thereof with methanol or isobutanol by established large-scale-industrial processes with formation of the fuel additive methyl tert-butyl ether (MTBE), or of the isobutyl tert-butyl ether that is used to obtain pure isobutene.

Raffinate II also comprises, alongside 1-butene and cis- and trans-2-butene, n- and isobutane, and residual amounts of up to 5% by weight of isobutene.

The dimerization of the linear butenes or of the butene mixture comprised in raffinate II can be carried out by means of the familiar processes used on a large industrial scale, for example those explained above in connection with the production of isoheptene mixtures, for example by means of heterogeneous, Brønsted-acid catalysts such as those used in the PolyGas® process or EMOGAS® process, by means of the Dimersol® process with use of nickel complex catalysts homogeneously dissolved in the reaction medium, or by means of heterogeneous, nickel(II)-oxide-containing catalysts by the Octol® process or by the process of WO 9514647. The resultant isooctene mixtures are converted to isononanal mixtures by the known processes explained above in connection with the production of heptanal isomer mixtures, by means of rhodium or cobalt-catalyzed hydroformylation, preferably cobalt-catalyzed hydroformylation. These are then hydrogenated to give the suitable isononanol mixtures, for example by means of one of the catalysts mentioned above in connection with the production of isoheptanol.

The resultant isononanol isomer mixtures can be characterized by way of their iso-index, which can be calculated from the degree of branching of the individual, isomeric isononanol components in the isononanol mixture multiplied by the percentage proportion of these in the isononanol mixture: by way of example, n-nonanol contributes the value 0 to the iso-index of an isononanol mixture, methyl-octanols (single branching) contribute the value 1, and dimethylheptanols (double branching) contribute the value 2. The higher the linearity, the lower is the iso-index of the relevant isononanol mixture. Accordingly, the iso-index of an isononanol mixture can be determined via gas-chromatographic separation of the isononanol mixture into its individual isomers and attendant quantification of the percentage quantitative proportion of these in the isononanol mixture, determined by standard methods of gas-chromatographic analysis. In order to increase the volatility of the isomeric nonanols and improve the gas-chromatographic separation of these, they are advantageously trimethylsilylated by means of standard methods, for example via reaction with N-methyl-N-trimethylsilyltrifluoracetamide, prior to gas-chromatographic analysis. In order to achieve maximum quality of separation of the individual components during gas-chromatographic analysis, it is preferable to use capillary columns with polydimethylsiloxane as stationary phase. Capillary columns of this type are obtainable commercially, and a little routine experimentation by the person skilled in the art is all that is needed in order to select, from the many different products available commercially, one that has ideal suitability for this separation task.

The isononanols used in the process of the invention are generally isononanols with an iso index of from 0.8 to 2, preferably from 1.0 to 1.8, and particularly preferably from 1.1 to 1.5, esterified or etherified, which can be produced by the abovementioned processes.

Possible compositions of the type of isononanol mixtures that can be used in the process of the invention are stated below merely by way of example, and it should be noted here that the proportions of the isomers individually listed within the isononanol mixture can vary, depending on the composition of the starting material, for example raffinate II, the composition of butenes in which can vary with the production process, and on variations in the production conditions used, for example in the age of the catalysts utilized, and conditions of temperature and of pressure, which have to be adjusted appropriately thereto.

By way of example, an isononanol mixture produced via cobalt-catalyzed hydroformylation and subsequent hydrogenation from an isooctene mixture produced with use of raffinate II as raw material by means of the catalyst and process in accordance with WO 9514647 can have the following composition:

from 1.73 to 3.73% by weight, preferably from 1.93 to 3.53% by weight, particularly preferably from 2.23 to 3.23% by weight of 3-ethyl-6-methylhexanol;
from 0.38 to 1.38% by weight, preferably from 0.48 to 1.28% by weight, particularly preferably from 0.58 to 1.18% by weight of 2,6-dimethylheptanol;
from 2.78 to 4.78% by weight, preferably from 2.98 to 4.58% by weight, particularly preferably from 3.28 to 4.28% by weight of 3,5-dimethylheptanol;
from 6.30 to 16.30% by weight, preferably from 7.30 to 15.30% by weight, particularly preferably from 8.30 to 14.30% by weight of 3,6-dimethylheptanol;
from 5.74 to 11.74% by weight, preferably from 6.24 to 11.24% by weight, particularly preferably from 6.74 to 10.74% by weight of 4,6-dimethylheptanol;
from 1.64 to 3.64% by weight, preferably from 1.84 to 3.44% by weight, particularly preferably from 2.14 to 3.14% by weight of 3,4,5-trimethylhexanol;
from 1.47 to 5.47% by weight, preferably from 1.97 to 4.97% by weight, particularly preferably from 2.47 to 4.47% by weight of 3,4,5-trimethylhexanol, 3-methyl-4-ethylhexanol and 3-ethyl-4-methylhexanol;
from 4.00 to 10.00% by weight, preferably from 4.50 to 9.50% by weight, particularly preferably from 5.00 to 9.00% by weight of 3,4-dimethylheptanol;
from 0.99 to 2.99% by weight, preferably from 1.19 to 2.79% by weight, particularly preferably from 1.49 to 2.49% by weight of 4-ethyl-5-methylhexanol and 3-ethylheptanol;
from 2.45 to 8.45% by weight, preferably from 2.95 to 7.95% by weight, particularly preferably from 3.45 to 7.45% by weight of 4,5-dimethylheptanol and 3-methyloctanol;
from 1.21 to 5.21% by weight, preferably from 1.71 to 4.71% by weight, particularly preferably from 2.21 to 4.21% by weight of 4,5-dimethylheptanol;
from 1.55 to 5.55% by weight, preferably from 2.05 to 5.05% by weight, particularly preferably from 2.55 to 4.55% by weight of 5,6-dimethylheptanol;
from 1.63 to 3.63% by weight, preferably from 1.83 to 3.43% by weight, particularly preferably from 2.13 to 3.13% by weight of 4-methyloctanol;
from 0.98 to 2.98% by weight, preferably from 1.18 to 2.78% by weight, particularly preferably from 1.48 to 2.48% by weight of 5-methyloctanol;
from 0.70 to 2.70% by weight, preferably from 0.90 to 2.50% by weight, particularly preferably from 1.20 to 2.20% by weight of 3,6,6-trimethylhexanol;
from 1.96 to 3.96% by weight, preferably from 2.16 to 3.76% by weight, particularly preferably from 2.46 to 3.46% by weight of 7-methyloctanol;
from 1.24 to 3.24% by weight, preferably from 1.44 to 3.04% by weight, particularly preferably from 1.74 to 2.74% by weight of 6-methyloctanol;
from 0.1 to 3% by weight, preferably from 0.2 to 2% by weight, particularly preferably from 0.3 to 1% by weight of n-nonanol;
from 25 to 35% by weight, preferably from 28 to 33% by weight, particularly preferably from 29 to 32% by weight of other alcohols having 9 and 10 carbon atoms; with the proviso that the entirety of the components mentioned gives 100% by weight.

In accordance with what has been said above, an isononanol mixture produced via cobalt-catalyzed hydroformylation and subsequent hydrogenation with use of an isooctene mixture produced by means of the PolyGas® process or EMOGAS® process with an ethylene-containing butene mixture as raw material can vary within the range of the compositions below, depending on the composition of the raw material and variations in the reaction conditions used:

from 6.0 to 16.0% by weight, preferably from 7.0 to 15.0% by weight, particularly preferably from 8.0 to 14.0% by weight of n-nonanol;
from 12.8 to 28.8% by weight, preferably from 14.8 to 26.8% by weight, particularly preferably from 15.8 to 25.8% by weight of 6-methyloctanol;
from 12.5 to 28.8% by weight, preferably from 14.5 to 26.5% by weight, particularly preferably from 15.5 to 25.5% by weight of 4-methyloctanol;
from 3.3 to 7.3% by weight, preferably from 3.8 to 6.8% by weight, particularly preferably from 4.3 to 6.3% by weight of 2-methyloctanol;
from 5.7 to 11.7% by weight, preferably from 6.3 to 11.3% by weight, particularly preferably from 6.7 to 10.7% by weight of 3-ethylheptanol;
from 1.9 to 3.9% by weight, preferably from 2.1 to 3.7% by weight, particularly preferably from 2.4 to 3.4% by weight of 2-ethylheptanol;

from 1.7 to 3.7% by weight, preferably from 1.9 to 3.5% by weight, particularly preferably from 2.2 to 3.2% by weight of 2-propylhexanol;

from 3.2 to 9.2% by weight, preferably from 3.7 to 8.7% by weight, particularly preferably from 4.2 to 8.2% by weight of 3,5-dimethylheptanol;

from 6.0 to 16.0% by weight, preferably from 7.0 to 15.0% by weight, particularly preferably from 8.0 to 14.0% by weight of 2,5-dimethylheptanol;

from 1.8 to 3.8% by weight, preferably from 2.0 to 3.6% by weight, particularly preferably from 2.3 to 3.3% by weight of 2,3-dimethylheptanol;

from 0.6 to 2.6% by weight, preferably from 0.8 to 2.4% by weight, particularly preferably from 1.1 to 2.1% by weight of 3-ethyl-4-methylhexanol;

from 2.0 to 4.0% by weight, preferably from 2.2 to 3.8% by weight, particularly preferably from 2.5 to 3.5% by weight of 2-ethyl-4-methylhexanol;

from 0.5 to 6.5% by weight, preferably from 1.5 to 6% by weight, particularly preferably from 1.5 to 5.5% by weight of other alcohols having 9 carbon atoms;

with the proviso that the entirety of the components mentioned gives 100% by weight.

Decanol

The alcohol component isodecanol used in the process of the invention is not a unitary chemical compound, but instead is a complex mixture of variously branched, isomeric decanols.

These are generally produced via nickel- or Brønsted-acid-catalyzed trimerization of propylene, for example by the PolyGas® process or the EMOGAS® process explained above, subsequent hydroformylation of the resultant isononene isomer mixture by means of homogeneous rhodium or cobalt carbonyl catalysts, preferably by means of cobalt carbonyl catalysts, and hydrogenation of the resultant isodecanal isomer mixture, e.g. by means of the catalysts and processes mentioned above in connection with the production of $C_7$-$C_9$-alcohols (Ullmann's Encyclopedia of Industrial Chemistry; 5$^{th}$ edition, vol. A1, p. 293, VCH Verlagsgesellschaft GmbH, Weinheim 1985). The resultant isodecanol generally has a high degree of branching.

The 2-propylheptanol used in the process of the invention can be pure 2-propylheptanol or can be a propylheptanol isomer mixture of the type formed during the industrial production of 2-propylheptanol and generally also called 2-propylheptanol.

Pure 2-propylheptanol can be obtained via aldol condensation of n-valeraldehyde and subsequent hydrogenation of the resultant 2-propylheptanal, for example in accordance with U.S. Pat. No. 2,921,089. By virtue of the production process, commercially obtainable 2-propylheptanol generally comprises, alongside the main component 2-propylheptanol, one or more of the following isomers of 2-propylheptanol: 2-propyl-4-methylhexanol, 2-propyl-5-methylhexanol, 2-isopropylheptanol, 2-isopropyl-4-methylhexanol, 2-isopropyl-5-methylhexanol, and/or 2-propyl-4,4-dimethylpentanol. The presence of other isomers of 2-propylheptanol, for example 2-ethyl-2,4-dimethylhexanol, 2-ethyl-2-methylheptanol, and/or 2-ethyl-2,5-dimethylhexanol, in the 2-propylheptanol is possible, but because the rates of formation of the aldehydic precursors of these isomers in the aldol condensation are low, the amounts of these present in the 2-propylheptanol are only trace amounts, if they are present at all, and they play practically no part in determining the plasticizer properties of the compounds produced from these 2-propylheptanol isomer mixtures.

Various hydrocarbon sources can be utilized as starting material for the production of 2-propylheptanol, for example 1-butene, 2-butene, raffinate I—an alkane/alkene mixture which is obtained from the $C_4$-cut of a cracker after removal of allenes, of acetylenes, and of dienes and which also comprises, alongside 1- and 2-butene, considerable amounts of isobutene—or raffinate II, which is obtained from raffinate I via removal of isobutene and then comprises, as olefin components other than 1- and 2-butene, only small proportions of isobutene. It is also possible, of course, to use mixtures of raffinate I and raffinate II as raw material for the production of 2-propylheptanol. These olefins or olefin mixtures can be hydroformylated by methods that are per se conventional with cobalt or rhodium catalysts, and 1-butene here gives a mixture of n- and isovaleraldehyde—the term isovaleraldehyde designating the compound 2-methylbutanal, the n/iso ratio of which can vary within relatively wide limits, depending on catalyst used and on hydroformylation conditions. By way of example, when a triphenylphosphine-modified homogeneous rhodium catalyst (Rh/TPP) is used, n- and isovaleraldehyde are formed in an n/iso ratio that is generally from 10:1 to 20:1 from 1-butene, whereas when rhodium hydroformylation catalysts modified with phosphite ligands are used, for example in accordance with U.S. Pat. No. 5,288,918 or WO 05028407, or when rhodium hydroformylation catalysts modified with phosphoamidite ligands are used, for example in accordance with WO 0283695, n-valeraldehyde is formed almost exclusively. While the Rh/TPP catalyst system converts 2-butene only very slowly in the hydroformylation, and most of the 2-butene can therefore be reclaimed from the hydroformylation mixture, 2-butene is successfully hydroformylated with the phosphite-ligand- or phosphorus amidite ligand-modified rhodium catalysts mentioned, the main product formed being n-valeraldehyde. In contrast, isobutene comprised within the olefinic raw material is hydroformylated at varying rates by practically all catalyst systems to 3-methylbutanal and, in the case of some catalysts, to a lesser extent to pivalaldehyde.

The $C_5$-aldehydes obtained in accordance with starting materials and catalysts used, i.e. n-valeraldehyde optionally mixed with isovaleraldehyde, 3-methylbutanal, and/or pivalaldehyde, can be separated, if desired, completely or to some extent by distillation into the individual components prior to the aldol condensation, and here again there is therefore a possibility of influencing and of controlling the composition of isomers of the $C_{10}$-alcohol component used in the production process of the invention. Equally, it is possible that the $C_5$-aldehyde mixture formed during the hydroformylation is introduced into the aldol condensation without prior isolation of individual isomers. If n-valeraldehyde is used in the aldol condensation, which can be carried out by means of a basic catalyst, for example an aqueous solution of sodium hydroxide or of potassium hydroxide, for example by the processes described in EP-A 366089, U.S. Pat. No. 4,426,524, or U.S. Pat. No. 5,434,313, 2-propylheptanal is produced as sole condensate, whereas if a mixture of isomeric $C_5$-aldehydes is used the product comprises an isomer mixture of the products of the homoaldol condensation of identical aldehyde molecules and of the crossed aldol condensation of different valeraldehyde isomers. The aldol condensation can, of course, be controlled via targeted reaction of individual isomers in such a way that a single aldol condensation isomer is formed predominantly or entirely. The relevant aldol condensates can then be hydrogenated with conventional hydrogenation catalysts, for example those mentioned above for the hydrogenation of aldehydes, to give the corresponding alcohols or alcohol mixtures, usually after preceding, preferably distillative isolation from the reaction mixture and, if desired, distillative purification.

The process of the invention generally uses mixtures of the 2-propylheptanol with the propylheptanol isomers mentioned in which the content of 2-propylheptanol is at least 50% by weight, preferably from 60 to 98% by weight, and particularly preferably from 80 to 95% by weight, in particular from 85 to 95% by weight.

Suitable mixtures of 2-propylheptanol with the propylheptanol isomers comprise by way of example those of from 60 to 98% by weight of 2-propylheptanol, from 1 to 15% by weight of 2-propyl-4-methylhexanol, and from 0.01 to 20% by weight of 2-propyl-5-methylhexanol, and from 0.01 to 24% by weight of 2-isopropylheptanol, where the sum of the proportions of the individual constituents does not exceed 100% by weight. It is preferable that the proportions of the individual constituents give a total of 100% by weight.

Other suitable mixtures of 2-propylheptanol with the propylheptanol isomers comprise by way of example those of from 75 to 95% by weight of 2-propylheptanol, from 2 to 15% by weight of 2-propyl-4-methylhexanol, from 1 to 20% by weight of 2-propyl-5-methylhexanol, from 0.1 to 4% by weight of 2-isopropylheptanol, from 0.1 to 2% by weight of 2-isopropyl-4-methylhexanol, and from 0.1 to 2% by weight of 2-isopropyl-5-methylhexanol, where the sum of the proportions of the individual constituents does not exceed 100% by weight. It is preferable that the proportions of the individual constituents give a total of 100% by weight.

Preferred mixtures of 2-propylheptanol with the propylheptanol isomers comprise those with from 85 to 95% by weight of 2-propylheptanol, from 5 to 12% by weight of 2-propyl-4-methylhexanol, and from 0.1 to 2% by weight of 2-propyl-5-methylhexanol, and from 0.01 to 1% by weight of 2-isopropylheptanol, where the sum of the proportions of the individual constituents does not exceed 100% by weight. It is preferable that the proportions of the individual constituents give a total of 100% by weight.

When said 2-propylheptanol isomer mixtures are used instead of pure 2-propylheptanol, the isomer composition of the alkyl ester groups of the products is practically the same as the composition of the propylheptanol isomer mixtures used for the esterification.

Undecanol

The undecanols used in the process of the invention can be straight-chain or branched, or can be composed of mixtures of straight-chain and branched undecanols. It is preferable to use, as alcohol component, mixtures of branched undecanols, also termed isoundecanol.

Substantially straight-chain undecanol can be obtained via rhodium- or preferably cobalt-catalyzed hydroformylation of 1-decene and subsequent hydrogenation of the resultant n-undecanal. The starting olefin 1-decene is produced by way of the SHOP process mentioned previously for the production of 1-octene.

For the production of branched isoundecanol, the 1-decene obtained in the SHOP process can be subjected to skeletal isomerization, for example by means of acidic zeolitic molecular sieves, as described in WO 9823566, whereupon mixtures of isomeric decenes are formed, rhodium- or preferably cobalt-catalyzed hydroformylation of which, with subsequent hydrogenation of the resultant isoundecanal mixtures, gives the isoundecanol used for the production of the compounds of the invention. Hydroformylation of 1-decene or of isodecene mixtures by means of rhodium or cobalt catalysis can be achieved as described previously in connection with the synthesis of $C_7$-$C_{10}$-alcohols. Similar considerations apply to the hydrogenation of n-undecanal or of isoundecanal mixtures to give n-undecanol and, respectively, isoundecanol.

After distillative purification of the hydrogenation product, the resultant $C_7$-$C_{11}$-alkyl alcohols or a mixture of these can be used in the process of the invention.

Dodecanol

Substantially straight-chain dodecanol can be obtained advantageously by way of the Alfol® process or Epal® process. These processes include the oxidation and hydrolysis of straight-chain trialkylaluminum compounds which are constructed stepwise by way of a plurality of ethylation reactions, starting from triethylaluminum, with use of Ziegler-Natta catalysts. The desired n-dodecanol can be obtained from the resultant mixtures of substantially straight-chain alkyl alcohols of varying chain length after distillative discharge of the $C_{12}$-alkyl alcohol fraction.

Alternatively, n-dodecanol can also be produced via hydrogenation of natural fatty acid methyl esters, for example from coconut oil.

Branched isododecanol can be obtained by analogy with the processes described previously for the codimerization and/or oligomerization of olefins with subsequent hydroformylation and hydrogenation of the isoundecene mixtures. After distillative purification of the hydrogenation product, the resultant isododecanols or mixtures of these, as described above, can be used in the process of the invention.

The carboxylic acids used in the process of the invention are selected from aromatic mono-, di-, tri-, or tetracarboxylic acids, aliphatic mono- and dicarboxylic acids, hydroxycarboxylic acids, alicyclic mono-, di-, tri-, and tetracarboxylic acids, heterocyclic dicarboxylic acids, the anhydrides of the abovementioned carboxylic acids, and mixtures thereof.

The aromatic mono-, di-, tri-, or tetracarboxylic acids and anhydrides of these used in the process of the invention are by way of example benzoic acid, benzoic anhydride, phthalic acid, phthalic anhydride, isophthalic acid, terephthalic acid, trimellitic acid, trimellitic anhydride, pyromellitic acid, and pyromellitic dianhydride.

The aliphatic mono- and dicarboxylic acids used in the process of the invention are by way of example saturated mono- and dicarboxylic acids such as acetic acid, butyric acid, valeric acid, succinic acid, adipic acid, or sebacic acid, saturated mono- and dicarboxylic acids such as acrylic acid, maleic acid, or fumaric acid, or else optionally the anhydrides of the abovementioned carboxylic acids.

The hydroxycarboxylic acids used in the process of the invention are by way of example glycolic acid, lactic acid, malic acid, tartaric acid, or citric acid, or else optionally anhydrides of these.

The alicyclic mono-, di-, tri-, and tetracarboxylic acids used in the process of the invention are by way of example the ring-hydrogenated derivatives of the abovementioned aromatic mono-, di-, tri-, or tetracarboxylic acids, an example being cyclohexanecarboxylic acid, 1,2-cyclohexanedicarboxylic acid, 1,3-cyclohexanedicarboxylic acid, 1,4-cyclohexanedicarboxylic acid, 1,2,4-cyclohexanedicarboxylic acid, or 1,2,4,5-cyclohexanetetracarboxylic acid, or else optionally anhydrides of these.

The heterocyclic dicarboxylic acids used in the process of the invention are by way of example 2,5-furandicarboxylic acid or 2,5-tetrahydrofurandicarboxylic acid.

In one preferred embodiment of the process of the invention, the carboxylic acid is selected from benzoic acid, benzoic anhydride, phthalic acid, phthalic anhydride, isophthalic acid, terephthalic acid, trimellitic acid, trimellitic anhydride, pyromellitic acid, and pyromellitic dianhydride. It is particularly preferable that the carboxylic acid is selected from benzoic acid, benzoic anhydride, terephthalic acid, trimellitic acid, trimellitic anhydride. In particular, terephthalic acid is used as carboxylic acid in the process of the invention.

Plasticizer Use

In plastics where optical properties are of prime importance it is generally desirable that the plasticizers used for production thereof have little intrinsic color, i.e. a low color value.

The carboxylic esters produced by the process of the invention feature in particular a low color value. They are therefore advantageously suitable for the use as plasticizers or in plasticizers for thermoplastic polymers and elastomers.

Furthermore, the use of high-purity methanesulfonic acid (Lutropur® MSA or Lutropur® MSA 100) as catalyst gives the carboxylic esters produced by the process of the invention low total chlorine content and also low sulfate content.

The carboxylic esters produced by the process of the invention can generally be used in all of the thermoplastically processible polymers produced with use of plasticizer. It is preferable that these thermoplastic polymers are selected from polyvinyl chloride (PVC), polyvinyl butyral (PVB), vinyl acetate homo- and copolymers, styrene homo- and copolymers, polyacrylates, thermoplastic polyurethanes (TPU), polysulfides, and mixtures thereof.

The carboxylic esters produced by the process of the invention can also be used in the production of elastomers. These are preferably natural rubber (NR) or rubbers produced synthetically, for example polyisoprene rubber (IR), styrene-butadiene rubber (SBR), butadiene rubber (BR), nitrile-butadiene rubber (NBR), or chloroprene rubber (CR).

The invention is explained in more detail with reference to the inventive examples described below. The inventive examples here are not to be interpreted as restricting the invention.

The examples and figures below use the following abbreviations: MSA for methanesulfonic acid,
PTSA for para-toluenesulfonic acid,
Basionics ST 35 for 1-ethyl-3-methylimidazolium methanesulfonate,
MSTFA for N-rnethyl-N-(trirmethylsilyl)trifluoroacetamide,
DOTP for bis(2-ethylhexyl) terephthalate (dioctyl terephthalate),
APHA for American Public Health Association.

EXAMPLES

I) Analytical Studies
I.a Gas-chromatographic Study:

For gas-chromatographic studies, an excess of MSTFA (N-methyl-N-(trimethylsilyl)trifluoroacetamide) was admixed with the samples, and the mixture was heated for 30 min to 100° C. so that all of the acidic protons had been converted to the appropriate trimethylsilyl groups. After cooling, the samples were diluted with N,N-dimethyl-formamide (DMF).

Data relating to the gas-chromatographic separation system and to the separation method:
Equipment: Agilent 6890 Series
Injector: split/splitless with split liner siltec-deactivated (Restec #20713-214.5)
Column: Optima 1 (length=25 m, internal diameter=0.25 mm, external diameter=0.40 mm, film thickness 0.25 μm) from Macherey & Nagel Detector: FID mit 300 ml/min of air, 30 ml/min of hydrogen and 30 ml/min of make-up gas (nitrogen)
Carrier gas: nitrogen
Flow rate: 0.7 ml/min at 8.3 psi (with oven temperature 80° C.)
Split: 1:36, split flow: 28 ml/min, septum purge 2.0 ml/min (with oven temperature 80° C.)
Injector temperature: 340° C.
Injection volume: 1 μl
Detector temperature: 320° C.
Temperature program:
  Start: 120° C.
  Residence time 1: 0 min
  Temperature gradient 1: 20° C./min
  Final temperature 1: 350° C.
  Residence time 2: 5 min
  Total running time: 16.5 min
When the samples comprise high boilers, residence time 2 can alternatively be set to 30 min. Total running time then increases to 41.5 min.
Evaluation: Empower-3 software using area %
Retention times:

| | |
|---|---|
| DOTP (peak 1) | 10.456 min (main peak) |
| DOTP (peak 2) | 10.202 min (isomer of peak 1) |
| 2-Ethyl-1-hexanol-MSTFA | 2.87 min |
| 2-Ethyl-1-hexyl mesylate | 4.44 min |
| Terephthalic-acid-MSTFA | 6.39 min |
| Monoester-MSTFA | 8.52 min |
| Ethylhexanol-di-ether | 4.89 min |

I.b Determination of Acid Number:

Acid number, stated in mg KOH/g of sample, is determined in propanol by potentiometric titration with 0.1 mol/L standard tetrabutylammonium hydroxide solution. Equipment and electrodes from Metrohm are used for the determination.

I.c Determination of APHA Hazen Color Value:

Hazen color value is measured by the method based on DIN/EN/ISO 6271-2 (March 2005) on undiluted material against water as reference. Round cells of diameter 11 mm are used. Equipment used can by way of example be a Dr. Lange LICO 400 photometer.

II) Production Examples:

Inventive Example 1

Synthesis of DOTP from terephthalic acid and 2-ethylhexanol with MSA as catalyst and 1-ethyl-3-methylimidazolium methanesulfonate (Basionics AT 35) as cosolvent.

Terephthalic acid (249 g, 1.50 mol), 2-ethylhexanol (469 g, 3.60 mol), and methanesulfonic acid (Lutropur MSA, BASF, 6.13 g of an approximately 70% by weight aqueous solution, 0.045 mol) and 1-ethyl-3-methylimidazolium methanesulfonate (Basionics ST 35, 55 g) are used as initial charge in a 1.6 L double-walled stirred-tank reactor which can be heated by way of a programmable thermostat and has anchor stirrer, Jennewein water separator, condenser, nitrogen inlet, and connection for a vacuum pump, and the reactor is inertized with nitrogen. The nitrogen flow rate through the apparatus was set to from 2 to 4 L h$^{-1}$, and the reaction mixture was heated to 180° C., whereupon an azeotropic mixture of water and 2-ethylhexanol was formed and liquefied in the condenser, and was passed through to the water separator. After phase separation, the organic phase was returned to the reactor, while the aqueous phase was discarded. The water removed was weighed and used to monitor the reaction. In order to ensure a constant flow of distillate, the temperature was increased within 3 h in stages to 200° C. and finally within a period of 1.5 h to 224° C. Thereafter both phases of the reaction mixture were present in the form of clear solutions. After a reaction time of 4.5 h, the conversion, based on the amount of water removed, was 90%. The reaction mixture was also studied by gas chromatography. Here it was found, surprisingly, that <1% of the amount of 2-ethylhexanol used had been lost to side reactions. After cooling to 80° C., the phases were separated and the ionic fraction (63 g), which as well as the ionic liquid also contained the catalyst and the unreacted terephthalic acid, was separated off and kept for recycling. The phase containing DOTP and 2-ethylhexanol was washed with 1.8% NaOH (25 g) and water (200 mL), and then the excess 2-ethylhexanol, and also all of the other compounds with a boiling point below the boiling point of DOTP, were drawn off in vacuo (220° C., 5 mbar). The resultant product was filtered through a pressure-filter funnel. Reaction time: 4.5 h. Yield: 85%. GC content: 98.77% of DOTP (area %). Color value (APAH, Hazen): 30.

Inventive Example 2

Synthesis of DOTP from terephthalic acid and 2-ethylhexanol with MSA as catalyst and the ionic phase from inventive example 1.

Terephthalic acid (249 g, 1.50 mol), 2-ethylhexanol (469 g, 3.60 mol) and the ionic fraction from inventive example 1 (55 g) are used as initial charge in a 1.6 L double-walled stirred-tank reactor which can be heated by way of a programmable thermostat and has anchor stirrer, Jennewein water separator, condenser, nitrogen inlet, and connection for a vacuum pump, and the reactor is inertized with nitrogen. The nitrogen flow rate through the apparatus was set to from 2 to 4 L h$^{-1}$, and the reaction mixture was heated to 180° C., whereupon an azeotropic mixture of water and 2-ethylhexanol was formed and liquefied in the condenser, and was passed through to the water separator. After phase separation, the organic phase was returned to the reactor, while the aqueous phase was discarded. The water removed was weighed and used to monitor the progress of the reaction. In order to ensure a constant flow of distillate, the temperature was increased within a period of 2 h in stages to 200° C. and finally within a period of 6 h to 217° C. Thereafter both phases of the reaction mixture were present in the form of clear solutions. After a reaction time of 8 h, the conversion, based on the amount of water removed, was 90%. The reaction mixture was also studied by gaschromatography. Here it was found, surprisingly, that only 0.56% of the amount of 2-ethylhexanol originally used had undergone decomposition to form the corresponding olefins. The losses due to formation of further secondary products (mesylates, ethers) ran at <0.5% of the amount of 2-ethylhexanol used. After cooling to 80° C., the phases were separated and the ionic fraction, which as well as the ionic liquid also contained the catalyst and the unreacted terephthalic acid, was separated off and kept for recycling. The phase containing DOTP and 2-ethylhexanol was washed with 1.8% NaOH (35 g) and water (300 ml), and then excess alcohol was removed by distillation (220° C., 8 mbar). The resultant product was filtered through a pressure-filter funnel. Reaction time: 8 h. Yield: 90%. HPLC content: 99.64% of DOTP (area %). Color value (APAH, Hazen): 85, acid number: 0.4 mg KOH/g.

Comparative Example CE3

Synthesis of DOTP from terephthalic acid and 2-ethylhexanol with MSA as catalyst without ionic liquid.

Terephthalic acid (249 g, 1.50 mol), 2-ethylhexanol (469 g, 3.60 mol), and methanesulfonic acid (Lutropur MSA, BASF, 6.13 g of an approximately 70% by weight aqueous solution, 0.045 mol) were used as initial charge in a 1.6 L double-walled stirred-tank reactor which can be heated by way of a programmable thermostat and has anchor stirrer, Jennewein water separator, condenser, nitrogen inlet, and connection for a vacuum pump, and the reactor was inertized with nitrogen. The nitrogen flow rate through the apparatus was set to from 2 to 4 L h$^{-1}$, and the reaction mixture was heated to 180° C., whereupon an azeotropic mixture of water and 2-ethylhexanol was formed and liquefied in the condenser, and was passed through to the water separator. After phase separation, the organic phase was returned to the reactor, while the aqueous phase was discarded. The water removed was weighed and used to monitor the reaction. In order to ensure a constant flow of distillate and to achieve full conversion in the reaction, the temperature was increased within a period of 4 h in stages to 200° C. and finally within a period of 2 h to 215° C. The temperature was kept there at that level until the reaction mixture was present as a clear solution and the calculated amount of water derived from the reaction and from the methanesulfonic acid used had been collected (56 g). The reaction time was 7.5 h. The reaction mixture was studied by gas chromatography. The losses due to formation of secondary products ran at about 5% of the amount of 2-ethylhexanol used.

Comparative Example CE4

Synthesis of DOTP from terephthalic acid and 2-ethylhexanol with tetraisopropyl titanate as catalyst and 1-ethyl-3-methylimidazolium methanesulfonate (Basionics ST 35) as cosolvent.

Terephthalic acid (249 g, 1.50 mol), 2-ethylhexanol (469 g, 3.60 mol), tetraisopropyl titanate (3.22 mmol) and 1-ethyl-3-methylimidazolium methanesulfonate (Basionics ST 35, 36 g) were used as initial charge in a 1.6 L double-walled stirred-tank reactor which can be heated by way of a programmable thermostat and has anchor stirrer, Jennewein water separator, condenser, nitrogen inlet, and connection for a vacuum pump, and the reactor was inertized with nitrogen. The nitrogen flow rate through the apparatus was set to from 2 to 4 L h$^{-1}$, and the reaction mixture was heated to 180° C., whereupon an azeotropic mixture of water and 2-ethylhexanol was formed, which liquified in the condenser and was passed through to the water separator. After phase separation, the organic phase was returned to the reactor, while the aqueous phase was discarded. The amount of water removed was weighed and used to monitor the progress of the reaction. In order to ensure a constant flow of distillate, the temperature was increased within a period of 2 h in stages to 200° C. and finally within a period of 6 h to 219° C. After 13 h, the reaction was showing incomplete conversion. The two phases could not be cleanly separated, and the catalyst could not be reused. The batch was discarded.

Comparative Example CE5

Synthesis of DOTP from terephthalic acid and 2-ethylhexanol with MSA as catalyst and butylpyridinium chloride as ionic liquid.

Terephthalic acid (249 g, 1.50 mol), 2-ethylhexanol (469 g, 3.60 mol), methanesulfonic acid (Lutropur MSA, BASF, 6.13 g of an approximately 70% by weight aqueous solution, 0.045 mol) and butylpyridinium chloride (36 g, 0.21 mol)

were used as initial charge in a 1.6 L double-walled stirred-tank reactor which can be heated by way of a programmable thermostat and has anchor stirrer, Jennewein water separator, condenser, nitrogen inlet and connection for a vacuum pump, and the reactor was inertized with nitrogen. The nitrogen flow rate through the apparatus was set to from 2 to 4 L h$^{-1}$, and the reaction mixture was heated to 180° C. When within a period of 5 h, besides the water present in the methanesulfonic acid solution, no further water had separated out, the batch was discarded.

Comparative Example CE6

Synthesis of DOTP from terephthalic acid and 2-ethylhexanol with dimethyltin dichloride as catalyst and butylpyridinium chloride as ionic liquid.

The experimental procedure was as for comparative example 5, but using dimethyltin dichloride (0.57 g, 2.57 mmol) as catalyst in place of the methanesulfonic acid. When within a period of 4 h no water had separated out, the batch was discarded.

The invention claimed is:

1. A process for the production of a carboxylic ester, comprising:
    reacting at least one carboxylic acid and/or at least one carboxylic anhydride, selected from aromatic mono-, di-, tri-, or tetracarboxylic acids, aliphatic mono- and dicarboxylic acids, hydroxycarboxylic acids, alicyclic mono-, di-, tri-, and tetracarboxylic acids, heterocyclic dicarboxylic acids, the anhydrides of the abovementioned carboxylic acids, and mixtures thereof,
    with
    at least one alcohol R$^1$—OH, in which R$^1$ is selected among unbranched and branched saturated C$_5$-C$_{13}$-alkyl moieties,
    with the proviso that the reaction takes place
        in the presence of at least one ionic liquid which is selected from among salts of the general formula (Ia),

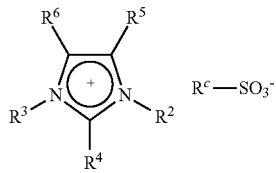

(Ia)

in which
    radicals R$^2$ and R$^3$, independently of one another, are hydrogen, unsubstituted or substituted alkyl, alkenyl, cycloalkyl, cycloalkenyl, aryl or heteroaryl,
    radicals R$^4$, R$^5$, and R$^6$, independently of one another, are hydrogen, unsubstituted or substituted alkyl, alkenyl, cycloalkyl, cycloalkenyl, heterocycloalkyl, aryl, heteroaryl or alkoxy,
    and
    R$^c$ is alkyl, cycloalkyl or aryl, where aryl may be substituted by 1, 2 or 3 alkyl radicals,
    in the presence of at least one catalyst selected among organic sulfonic acids, wherein the at least one catalyst is not covalently attached to the ionic liquid of the general formula (Ia), and
    with distillative removal, in the form of an azeotropic mixture with the alcohol R$^1$—OH used, of at least one portion of the water formed during the reaction,
    where at least to some extent the alcohol R$^1$—OH removed by distillation is returned to the reaction system.

2. The process according to claim 1, wherein the reaction takes place with supply to the reaction system of a gas which is inert under the reaction conditions.

3. The process according to claim 1, wherein the reaction takes place at a reaction mixture temperature of 60 -250° C.

4. The process according to claim 1, wherein the anion of the at least one ionic liquid corresponds to the deprotonated form of the organic sulfonic acid used as catalyst.

5. The process according to claim 2, wherein the reaction of at least one carboxylic acid and/or of at least one carboxylic anhydride and of at least one alcohol R$^1$—OH is carried out in at least one reactor, where the inert gas is passed into the at least one reactor below the liquid surface, and the inert gas is bubbled through the reaction mixture.

6. The process according to claim 2, where the reaction takes place in a cascade made of at least two reactors.

7. The process according to claim 6, where the inert gas is introduced at least into the first reactor of the cascade.

8. The process according to claim 1, wherein the reaction is carried out continuously.

9. The process according to claim 1, wherein the radical R$^1$ is n-octyl, 2-ethylhexyl, n-nonyl, isononyl, isodecyl, 2-propylheptyl, n-undecyl, or isoundecyl.

10. The process according to claim 1, wherein 2-ethylhexanol is used as alcohol R$^1$—OH.

11. The process according to claim 1, wherein the at least one carboxylic acid is at least one of benzoic acid, benzoic anhydride, phthalic acid, phthalic anhydride, isophthalic acid, terephthalic acid, trimellitic acid, trimellitic anhydride, pyromellitic acid, and pyromellitic dianhydride.

12. The process according to claim 1, for the production of bis(2-ethylhexyl) terephthalate by reaction of terephthalic acid with 2-ethylhexanol.

13. The process according to claim 1, wherein the at least one alcohol R$^1$—OH is present in a 1.01- to 2.0-fold molar excess, based on the carboxylic acid equivalents of the carboxylic acid material used.

14. The process according to claim 1, wherein the catalyst comprises at least one alkylsulfonic acid.

15. The process according to claim 1, wherein methanesulfonic acid is used as catalyst.

16. The process according to claim 1, wherein the amount used of the catalyst, based on the number of the carboxylic acid groups to be reacted, is from 0.5 to 5 mol %.

17. The process according to claim 1, wherein the fraction of the ionic liquid in the reaction mixture is from 1 to 50% by weight, based on the total weight of the reaction mixture.

18. The process according to claim 1, wherein, after the reaction has ended, an ionic fraction which comprises the ionic liquid, the at least one catalyst and also any unreacted carboxylic acid and/or unreacted carboxylic anhydride is removed from the reaction mixture and used again for further esterification reactions.

19. The process according to claim 1, wherein the catalyst consists of at least one alkylsulfonic acid.

* * * * *